US009554697B2

(12) United States Patent
Padrick et al.

(10) Patent No.: US 9,554,697 B2
(45) Date of Patent: *Jan. 31, 2017

(54) DETERMINATION OF THE EFFECTIVE LENS POSITION OF AN INTRAOCULAR LENS USING APHAKIC REFRACTIVE POWER

(71) Applicant: WaveTec Vision Systems, Inc., Aliso Viejo, CA (US)

(72) Inventors: Thomas D. Padrick, Seattle, WA (US); Jack T. Holladay, Bellaire, TX (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/320,377

(22) Filed: Jun. 30, 2014

(65) Prior Publication Data
US 2015/0092158 A1    Apr. 2, 2015

Related U.S. Application Data

(63) Continuation of application No. 12/835,668, filed on Jul. 13, 2010, now Pat. No. 8,764,187.
(Continued)

(51) Int. Cl.
A61B 3/103    (2006.01)
A61B 3/10     (2006.01)
(Continued)

(52) U.S. Cl.
CPC ............... *A61B 3/10* (2013.01); *A61B 3/0025* (2013.01); *A61B 3/103* (2013.01); *A61B 3/1015* (2013.01);
(Continued)

(58) Field of Classification Search
None
See application file for complete search history.

(56) References Cited

U.S. PATENT DOCUMENTS 4,019,813 A    4/1977    Cornsweet et al.
4,125,320 A    11/1978   Rassow
(Continued)

FOREIGN PATENT DOCUMENTS

AU    2005234778      8/2011
CN    2010-80040737.6  6/2011
(Continued)

OTHER PUBLICATIONS

Combined International Search Report and Written Opinion of the International Searching Authority for International Application No. PCT/US05/13550; issued by the ISA/US; dated Nov. 15, 2005.
(Continued)

*Primary Examiner* — Zachary Wilkes
(74) *Attorney, Agent, or Firm* — Baker Botts L.L.P.

(57) ABSTRACT

An ophthalmic method for determining a relationship between aphakic ocular power and estimated effective lens position (ELP) of an intraocular lens (IOL) to be implanted in a patient's eye. The method can be used to determine an estimate of the ELP of an IOL given the aphakic ocular power of the patient's eye, for example, without measurement of the corneal curvature or axial length of the patient's eye. The estimate of ELP can then be used to determine a suitable value of optical power for the IOL to be implanted in the patient's eye.

22 Claims, 8 Drawing Sheets

Related U.S. Application Data

(60) Provisional application No. 61/225,532, filed on Jul. 14, 2009.

(51) Int. Cl.
  *G02C 7/02* (2006.01)
  *A61F 2/16* (2006.01)
  *A61B 3/00* (2006.01)

(52) U.S. Cl.
  CPC ............... *A61F 2/16* (2013.01); *G02C 7/022* (2013.01); *G02C 7/024* (2013.01); *A61F 2/1662* (2013.01)

(56) References Cited

U.S. PATENT DOCUMENTS

| | | |
|---|---|---|
| 4,172,662 A | 10/1979 | Vogel |
| 4,173,398 A | 11/1979 | Okamoto et al. |
| 4,293,198 A | 10/1981 | Kohayakawa et al. |
| 4,353,625 A | 10/1982 | Nohda et al. |
| 4,372,655 A | 2/1983 | Matsumura et al. |
| 4,376,573 A | 3/1983 | Matsumura et al. |
| 4,390,255 A | 6/1983 | Nohda et al. |
| 4,421,391 A | 12/1983 | Matsumura et al. |
| 4,459,027 A | 7/1984 | Kafri et al. |
| 4,541,697 A | 9/1985 | Ramijan |
| 4,640,596 A | 2/1987 | Humphrey |
| 4,650,301 A | 3/1987 | Humphrey |
| 4,669,835 A | 6/1987 | Humphrey |
| 4,692,003 A | 9/1987 | Adachi et al. |
| 4,710,193 A | 12/1987 | Volk |
| 4,721,379 A | 1/1988 | L'Esperance |
| 4,730,917 A | 3/1988 | Krueger |
| 4,911,711 A | 3/1990 | Telfair et al. |
| 4,964,715 A | 10/1990 | Richards |
| 4,984,883 A | 1/1991 | Winocur |
| 4,995,716 A | 2/1991 | Warnicki et al. |
| 5,080,477 A | 1/1992 | Adachi |
| 5,144,478 A | 9/1992 | Toshimitsu |
| 5,157,427 A | 10/1992 | Humphrey |
| 5,164,750 A | 11/1992 | Adachi |
| 5,206,672 A | 4/1993 | Rowe |
| 5,208,619 A | 5/1993 | Campbell |
| 5,223,863 A | 6/1993 | Heine |
| 5,252,999 A | 10/1993 | Sukigara |
| 5,258,791 A | 11/1993 | Penney et al. |
| 5,270,749 A | 12/1993 | Okumura |
| 5,282,852 A | 2/1994 | Capetan et al. |
| 5,294,971 A | 3/1994 | Braunecker et al. |
| 5,307,097 A | 4/1994 | Baker |
| 5,329,322 A | 7/1994 | Yancey |
| 5,374,193 A | 12/1994 | Trachtman |
| 5,450,143 A | 9/1995 | Rowe et al. |
| 5,455,645 A | 10/1995 | Berger et al. |
| 5,493,109 A | 2/1996 | Wei et al. |
| 5,576,780 A | 11/1996 | Yancey |
| 5,777,719 A | 7/1998 | Williams et al. |
| 5,796,463 A | 8/1998 | Bullimore |
| 5,800,533 A | 9/1998 | Eggleston et al. |
| 5,861,937 A | 1/1999 | Fujieda |
| 5,909,268 A | 6/1999 | Isogai et al. |
| 5,936,706 A | 8/1999 | Takagi |
| 5,949,521 A | 9/1999 | Williams et al. |
| 5,963,300 A | 10/1999 | Horwitz |
| 5,968,094 A | 10/1999 | Werblin et al. |
| 5,968,095 A | 10/1999 | Norrby |
| 5,994,687 A | 11/1999 | Chanteloup et al. |
| 6,002,484 A | 12/1999 | Rozema et al. |
| 6,004,313 A | 12/1999 | Shimmick et al. |
| 6,007,204 A | 12/1999 | Fahrenkrug et al. |
| 6,042,232 A | 3/2000 | Luce et al. |
| 6,043,885 A | 3/2000 | Mazuet et al. |
| 6,050,687 A | 4/2000 | Bille et al. |
| 6,086,204 A | 7/2000 | Magnante |
| 6,095,651 A | 8/2000 | Williams et al. |
| 6,096,077 A | 8/2000 | Callahan et al. |
| 6,155,684 A | 12/2000 | Bille et al. |
| 6,199,986 B1 | 3/2001 | Williams et al. |
| 6,251,101 B1 | 6/2001 | Glockler |
| 6,262,328 B1 | 7/2001 | Wicks et al. |
| 6,264,328 B1 | 7/2001 | Williams et al. |
| 6,270,221 B1 | 8/2001 | Liang et al. |
| 6,271,915 B1 | 8/2001 | Frey et al. |
| 6,275,718 B1 | 8/2001 | Lempert |
| 6,299,311 B1 | 10/2001 | Williams et al. |
| 6,299,618 B1 | 10/2001 | Sugiura |
| 6,338,559 B1 | 1/2002 | Williams et al. |
| 6,379,005 B1 | 4/2002 | Williams et al. |
| 6,382,793 B1 | 5/2002 | Lai et al. |
| 6,382,794 B1 | 5/2002 | Lai et al. |
| 6,382,795 B1 | 5/2002 | Lai |
| 6,394,605 B1 | 5/2002 | Campin et al. |
| 6,409,345 B1 | 6/2002 | Molebny et al. |
| 6,419,671 B1 | 7/2002 | Lemberg |
| 6,439,720 B1 | 8/2002 | Graves et al. |
| 6,460,997 B1 | 10/2002 | Frey et al. |
| 6,497,483 B2 | 12/2002 | Frey et al. |
| 6,508,812 B1 | 1/2003 | Williams et al. |
| 6,550,917 B1 | 4/2003 | Neal et al. |
| 6,561,648 B2 | 5/2003 | Thomas |
| 6,570,143 B1 | 5/2003 | Neil et al. |
| 6,572,230 B2 | 6/2003 | Levine |
| 6,575,572 B2 | 6/2003 | Lai et al. |
| 6,578,963 B2 | 6/2003 | Pettit |
| 6,585,723 B1 | 7/2003 | Sumiya |
| 6,588,902 B2 | 7/2003 | Isogai |
| 6,598,975 B2 | 7/2003 | Liang et al. |
| 6,601,956 B1 | 8/2003 | Jean et al. |
| 6,609,793 B2 | 8/2003 | Norrby et al. |
| 6,609,794 B2 | 8/2003 | Levine |
| 6,626,535 B2 | 9/2003 | Altmann |
| 6,626,538 B1 | 9/2003 | Arrowsmith |
| 6,634,751 B2 | 10/2003 | Turner et al. |
| 6,637,884 B2 | 10/2003 | Martino |
| 6,658,282 B1 | 12/2003 | Eagan et al. |
| 6,679,606 B2 | 1/2004 | Campin et al. |
| 6,685,319 B2 | 2/2004 | Watson et al. |
| 6,702,806 B2 | 3/2004 | Gray et al. |
| 6,705,729 B2 | 3/2004 | Piers et al. |
| 6,724,464 B2 | 4/2004 | Yang et al. |
| 6,736,509 B2 | 5/2004 | Martino et al. |
| 6,736,510 B1 | 5/2004 | Van Heugten |
| 6,739,721 B2 | 5/2004 | Altmann |
| 6,761,454 B2 | 7/2004 | Lai et al. |
| 6,781,681 B2 | 8/2004 | Horwitz |
| 6,786,603 B2 | 9/2004 | Altmann |
| 6,793,654 B2 | 9/2004 | Lemberg |
| 6,819,413 B2 | 11/2004 | Neal et al. |
| 6,827,444 B2 | 12/2004 | Williams et al. |
| 6,836,374 B2 | 12/2004 | Esch et al. |
| 6,905,641 B2 | 6/2005 | Platt et al. |
| 6,908,196 B2 | 6/2005 | Herekar et al. |
| 6,926,710 B2 | 8/2005 | Cox et al. |
| 6,948,818 B2 | 9/2005 | Williams et al. |
| 6,997,555 B2 | 2/2006 | Dick et al. |
| 7,018,376 B2 | 3/2006 | Webb et al. |
| 7,034,949 B2 | 4/2006 | Horwitz |
| 7,044,602 B2 | 5/2006 | Chernyak |
| 7,044,604 B1 | 5/2006 | Arrowsmith |
| 7,057,806 B2 | 6/2006 | Atkinson |
| 7,066,928 B2 | 6/2006 | Dick et al. |
| 7,068,439 B2 | 6/2006 | Esch et al. |
| 7,070,276 B2 | 7/2006 | Koretz |
| 7,077,522 B2 | 7/2006 | Williams |
| 7,111,938 B2 | 9/2006 | Andino et al. |
| 7,182,780 B2 | 2/2007 | Terwee et al. |
| 7,237,898 B1 | 7/2007 | Hohla et al. |
| 7,255,442 B2 | 8/2007 | Bucourt et al. |
| 7,303,281 B2 | 12/2007 | Wakil et al. |
| 7,336,371 B1 | 2/2008 | Haidner et al. |
| 7,341,348 B2 | 3/2008 | Eagan |
| 7,350,916 B2 | 4/2008 | Hong et al. |
| 7,350,920 B2 | 4/2008 | Levine |
| 7,357,509 B2 | 4/2008 | Williams et al. |

(56) References Cited

U.S. PATENT DOCUMENTS

| | | |
|---|---|---|
| 7,377,641 B2 | 5/2008 | Piers et al. |
| 7,380,942 B2 | 6/2008 | Molebny et al. |
| 7,401,919 B2 | 7/2008 | Vogelsang et al. |
| 7,406,263 B2 | 7/2008 | Graves et al. |
| 7,416,305 B2 | 8/2008 | Williams et al. |
| 7,425,067 B2 | 9/2008 | Warden et al. |
| 7,441,901 B2 | 10/2008 | Liang |
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |
| 8,313,196 B2 | 11/2012 | Ianchulev |
| 8,333,474 B2 | 12/2012 | Michaels et al. |
| 8,394,083 B2 | 3/2013 | Van Heugten et al. |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli et al. |
| 2005/0105044 A1 | 5/2005 | Warden et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1 | 1/2006 | Mayo et al. |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0236702 A1 | 10/2007 | Neal et al. |
| 2007/0260157 A1 | 11/2007 | Norrby |
| 2008/0004610 A1 | 1/2008 | Miller et al. |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0009717 A1 | 1/2009 | Barrett et al. |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels et al. |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0036386 A1 | 2/2010 | Ianchulev |
| 2010/0042210 A1 | 2/2010 | Ianchulev |
| 2011/0001960 A1 | 1/2011 | Van Heugten |
| 2011/0015541 A1 | 1/2011 | Padrick |
| 2011/0267579 A1 | 11/2011 | Van Heugten |
| 2012/0147460 A1 | 6/2012 | Kubler |
| 2013/0021574 A1 | 1/2013 | Van Heugten |
| 2013/0070203 A1 | 3/2013 | Michaels |

FOREIGN PATENT DOCUMENTS

| | | |
|---|---|---|
| DE | 43 10 561 A1 | 9/1994 |
| EP | 0931504 A1 | 7/1999 |
| EP | 2444021 | 4/2012 |
| EP | 2453822 | 5/2012 |
| EP | 2453823 | 5/2012 |
| EP | 1596710 | 1/2013 |
| GB | 1 209 451 | 10/1970 |
| IL | 138282 | 7/2004 |
| JP | 11-24434 | 5/1989 |
| JP | 9-122075 | 5/1997 |
| JP | 10-272100 | 10/1998 |
| JP | 2000-139996 | 5/2000 |
| JP | 2001-507258 A | 6/2001 |
| JP | 2001-314372 A | 11/2001 |
| JP | 2002-306418 A | 10/2002 |
| JP | 2003-509731 A | 3/2003 |
| JP | 2003-102689 A | 4/2003 |
| JP | 4972546 | 4/2012 |
| WO | WO 92/01417 | 2/1992 |
| WO | WO 96/22506 | 7/1996 |
| WO | WO 98/27863 | 7/1998 |
| WO | WO 01/06914 | 2/2001 |
| WO | WO 01/21061 | 3/2001 |
| WO | WO 01/26591 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 | 6/2003 |
| WO | WO 03/102498 | 12/2003 |
| WO | WO 2004/093663 | 11/2004 |
| WO | WO 2005/057252 | 6/2005 |
| WO | WO 2006/081031 | 8/2006 |
| WO | WO 2009/086059 | 7/2009 |

OTHER PUBLICATIONS

Restriction Requirement issued on Apr. 10, 2007 in U.S. Appl. No. 10/820,635, filed Apr. 8, 2004.

(56) References Cited

OTHER PUBLICATIONS

Response to Restriction Requirement filed on May 3, 2007, in U.S. Appl. No. 10/820,635, filed Apr. 8, 2004.
Non-Final Office Action issued on Jul. 11, 2007 in U.S. Appl. No. 10/820,635, filed Apr. 8, 2004.
Office Action Response filed on Jan. 11, 2008 U.S. Appl. No. 10/820,635, filed Apr. 8, 2004.
Final Office Action issued on Apr. 10, 2008 in U.S. Appl. No. 10/820,635, filed Apr. 8, 2004.
Office Action mailed May 30, 2008 in Chinese Patent Application 200580011803.6 filed Apr. 20, 2005.
Request for Continued Examination and Amendment filed on May 11, 2009 in U.S. Appl. No. 10/820,635, filed Apr. 8, 2004.
Office Action mailed May 22, 2009 in Chinese Patent Application 200580011803.6 filed Apr. 20, 2005.
Notice of Allowance issued on May 26, 2009 in U.S. Appl. No. 10/820,635, filed Apr. 8, 2004.
Office Action mailed Jun. 2, 2009, issued in U.S. Appl. No. 11/110,653, filed Apr. 20, 2005.
Office Action mailed Jul. 7, 2009, in U.S. Appl. No. 11/110,968, filed Apr. 20, 2005.
Office Action issued on Sep. 10, 2010 in in U.S. Appl. No. 12/499,079, filed Jul. 7, 2009.
Preliminary Amendment filed Oct. 15, 2009 in U.S. Appl. No. 12/499,079, filed Jul. 7, 2009.
Office Action Response filed Dec. 1, 2009 in U.S. Appl. No. 11/110,653, filed Apr. 20, 2005.
Office Action mailed Dec. 25, 2009 in Chinese Patent Application 200580011803.6 filed Apr. 20, 2005.
Office Action Response filed Jan. 7, 2010 in U.S. Appl. No. 11/110,968, filed Apr. 20, 2005.
Office Action mailed Jan. 15, 2010, issued in European Application No. 05737636.0 filed Apr. 20, 2005.
Final Office Action mailed Feb. 1, 2010 in U.S. Appl. No. 11/110,653, filed Apr. 20, 2005.
Office Action issued on Apr. 6, 2010 in corresponding Australian Patent Application No. 2005234778.
RCE and Amendment filed Jul. 30, 2010 in U.S. Appl. No. 11/110,653, filed Apr. 20, 2005.
Notice of Allowance issued Sep. 28, 2010 in U.S. Appl. No. 11/110,653, filed Apr. 20, 2005.
International Search Report and Written Opinion mailed Oct. 7, 2010 for International Application No. PCT/US2010/041229.
Final Office Action mailed Oct. 29, 2010 in U.S. Appl. No. 11/110,968, filed Apr. 20, 2005.
Office Action dated Nov. 2, 2010 in Japanese Application No. 2007-509613 (with English Translation).
Office Action mailed Feb. 28, 2011 in U.S. Appl. No. 12/581,061, filed Oct. 16, 2009.
Amendment filed on Mar. 9, 2011 in U.S. Appl. No. 12/499,079, filed Jul. 7, 2009.
Notice of Allowance issued on Mar. 22, 2011 in U.S. Appl. No. 12/499,079, filed Jul. 7, 2009.
Response to Office Action mailed on Apr. 5, 2011 in corresponding Australian Patent Application No. 2005234778.
Request for Continued Examination, Final Amendment and Summary of Interview, filed in corresponding U.S. Appl. No. 11/110,968 on Apr. 29, 2011.
Response to Office Action filed in corresponding U.S. Appl. No. 12/581,061 on Jun. 28, 2011.
Preliminary Amendment filed Jul. 19, 2011 in corresponding U.S. Appl. No. 13/021,594.
Final Office Action issued on Sep. 6, 2011 in corresponding U.S. Appl. No. 12/581,061.
Notification of Reasons for Refusal mailed in corresponding Japanese Patent Application No. JP 2007-509613 on Oct. 11, 2011.
Office Action issued in corresponding European Patent Application No. 05737636 on Oct. 27, 2011.
Office Action issued on Jan. 17, 2012 in connection with Canadian Patent Application No. 2,515,010.
Office Action mailed on Jan. 25, 2012 in corresponding U.S. Appl. No. 13/021,594, filed Feb. 4, 2011.
Request for Continued Examination, Amendment and Terminal Disclaimer filed in connection with U.S. Appl. No. 12/581,061 on Mar. 5, 2012.
Decision to Grant issued on Mar. 13, 2012 in connection with Japanese Patent Application No. 2007-509613.
Notice of Allowance issued on Mar. 20, 2011 in connection with U.S. Appl. No. 12/581,061 on Mar. 5, 2012.
Extended Search Report issued on Mar. 26, 2012 in connection with European Patent Application No. 12151139.8.
Office Action issued on Mar. 26, 2012 in connection with European Application No. EP 05737636.
Response to Office Action filed on May 22, 2012 in corresponding U.S. Appl. No. 13/021,594.
Notice of Allowance issued on Jul. 11, 2012 in corresponding U.S. Appl. No. 13/021,594.
Notice of Allowance issued on Jul. 18, 2012 in corresponding U.S. Appl. No. 12/581,061.
Preliminary Amendment filed on Sep. 14, 2012 in corresponding U.S. Appl. No. 13/750,080.
Request for Continued Examination filed on Oct. 10, 2012 in corresponding U.S. Appl. No. 13/021,594.
Office Action issued on Oct. 25, 2012 in connection with corresponding U.S. Appl. No. 12/581,074.
Office Action issued on Oct. 26, 2012 in connection with corresponding U.S. Appl. No. 13/619,168.
Notice of Allowance issued on Oct. 30, 2012 in connection with corresponding U.S. Appl. No. 13/021,594.
Extended Search Report issued on Jan. 8, 2013 in connection with European Patent Application No. 10800335.
Response to Office Action filed Jan. 25, 2013 in connection with related U.S. Appl. No. 12/581,074.
Response to Office Action filed Jan. 28, 2013 in connection with related U.S. Appl. No. 13/619,168.
Terminal Disclaimer and Interview Summary submitted on Feb. 27, 2013 in corresponding U.S. Appl. No. 13/619,168.
Office Action issued May 9, 2013 in connection with U.S. Appl. No. 12/581,074.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations," http://doctor-hill.com/iol-mail/piggyback.html, accessed on Feb. 12, 2010.
Aramberri, "Intraocular lens power calculation after corneal infrastructure surgery: Double-K method," J Cataract Refract Surg 29:2063-2068 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "The Optical Design of the Intraocular Lens Implants," Opthalmic Surg 6(3): 17-31 (1975).
Brandser R., "Accuracy of IOL calculation in cataract surgery", Acta Ophthalmol Scand. Apr. 1997; 75(2):162-5 (Abstract).
Castro et al., "Tilt and decentration of intraocular lenses in vivo from Purkinje and Scheimpflug imaging: Validation study," J. Cataract Refract. Surg. 2007; 33:418-429.
Chen et al., "Analysis of intraocular lens power calculation in post-radial keratotomy eyes," J Cataract Refract Surg 29:65-? (Jan. 2003).
Colenbrander, "Calculation of the Power of an Iris-Clip Lens for Distance Vision," Br. J. Ophthal. 57:735-40(1973).
Cordonnier, M., et al., "How accurate is the hand-held refractor Retinomax(R) in measuring cycloplegic refraction: a further evaluation", Strabismus. Sep. 1998;6(3):133-142 (Abstract).
Cua et al., Intraocular lens calculations in patients with corneal scarring and irregular astigmatism, J Cataract Refract Surg 29:1352-1357 (Jul. 2003).
Donoso R., et al., "Emmetropization at cataract surgery. Looking for the best IOL power calculation formula according to the eye length", Arch Soc Esp Oftalmol. Sep. 2003;78(9):477-80 (Abstract).

(56) References Cited

OTHER PUBLICATIONS

El-Baha SM, et al., "Intraoperative biometry for intraocular lens (IOL) power calculation at silicone oil removal", Eur J Ophthalmol. Aug.-Sep. 2003;13(7):622-6. (Abstract).
El-Defrawy S., et al. "Evaluation of a hand-held autorefractor in children younger than 6", J Pediatr Ophthalmol Strabismus. ~ar-Apr. 1998;35(2):107-9 (Abstract).
Feiz, et al., "Intraocular Lens Power Calculation After Laser in Situ Keratomileusis for Myopia and Hyperopia—A Standard Approach," Cornea 20(8):792-797 (2001).
Feordorov et al. "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia. 2003;56(1):11-4 (Abstract).
Gernet, "IOL Calculation According to Gernet and the GOW 70 PC Programme," Abstract from Ophthalmologe 98:873-876 (2001).
Gimbel et al., "Accuracy and Predictability of Intraocular Lens Power Calculation After Laser in Situ Keratomileusis," J Cataract Refract Surg 27:571-576 (Apr. 2001).
Gimbel et al., "Accuracy and Predictability of Intraocular Lens Power Calculation After photorefractive keratectomy," J Cataract Refract Surg 26:1147-1151 (Apr. 2000).
Gupta, et al., *"Design and use of an infrared Pupilometer for real-time pupil mapping in response to incremental illumination levels,"* 2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/Article Standard/Article/detail/559856.
Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden lntraokularlinse" [Intraoperative retinoscopy for determining the refractive value of an implantable intraocular lens] Klin. Monatsbl. Augenheilkd. vol. 210, No. 4, 1997, pp. 207-212.
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," J. Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions. CLAO J. 1984, 10:326-31.
Holladay, JT, et al. "Calculating the Surgically Induced Refractive Change Following Ocular Surgery", J. Cataract Refract. Surg. 1992; 18:429-43.
Hunt et al., "Evaluation of the measurement of refractive error by the PowerRefractor: a remote, continuous and binocular measurement system of oculomotor function," Br. J. Opthalmol 87:1504-1508 (2003).
Ianchulev, "Method for Intraoperative Refractive IOL Calculation," Poster Presentation at Ophthalmology Conference (Apr. 2004).
Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536, Abstract.

Isenberg et al., "Use of the HARK Autorefractor in Children," American Journal of Ophthalmology 131(4):438-441 (2001).
Iuorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).
Ivanov MN, et al., "Formula for calculating the IOL focal power", Vestn Oftalmol. Jul.-Aug. 2003;119 (4):52-4 (Abstract).
Iwami S. et al., "Prediction of Postoperative Refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and LASIK", Korean J Ophthalmol. Jun. 2002;16(1):26-31 (Abstract).
Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).
Liang, et al. "Aberrations and Retinal Image Quality of the Normal Human Eye", J. Optical Society of America, vol. 14, No. 11, Nov. 1997.
Liang, et al. "Comparison of Measurements of Refractive Errors Between the Hand-held Retinomax and On-table Autorefractors in Cyclopleged and Noncyclopleged Children," American Journal of Ophthalmology 136(6): 1120-1128 (Dec. 2003).
Lipatov DV., "Assessment of the efficiency of different formulae applied to calculating the optic power of an intraocular lens in trans-scleral fixation", Vestn Oftalmol, Nov.-Dec. 2003;119(6):33-5 (Abstract).
Ma, et al., "Simple method for accurate alignment in toric phakic and aphakic intraocular lens implantation," J Cataract Refract Surg, Technique, Oct. 2008, vol. 34, pp. 1631-1636.
Mackool RJ., "The cataract extraction-refraction-implantation technique for IOL power calculation in difficult cases", J Cataract Refract Surg. Apr. 1998;24(4):434-5 (Abstract).
Masket, et al., "Atlas of Cataract Surgery," Book cover in 1 page, Front Matter in 11 pages (Table of Contents in 3 pages), Chapter 19 pp. 147-158, Published by Martin Dunitz Ltd 1999, United Kingdom.
Methling D, Kalb G., "A New Program for Calculating Intraocular Lenses", Klin Monatsbl Augenheilkd. Oct. 1992;201 (4):247-53 (Abstract).
Moreno-Barriuso, et al., "Laser Ray Tracing Versus Hartmann-Shack Sensor for Measuring Optical Aberrations in the Human Eye", J. Optical Society of America, vol. 17, No. 6, Jun. 2000.
Nemeth et al., "Optical and ultrasound measurement of axial length and anterior chamber depth for intraocular lens power calculation," J Cataract Refract Surg 29:85-88 (Jan. 2003).
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001).
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Photograph of Oculus Instrument, accessed at http://www.oculus.de/en/sites/popup_bild_gross.php?news=&id=1056 on Apr. 29, 2011.
Quiroga, et al., *"Fourier transform method for automatic processing of moire deflectograms,"* Jun. 1999, Society of Photo-Optical Instrumentation Engineers, pp. 974-982.
Raj et al., "Clinical evaluation of automated refractio in anterior chamber pseudophakia," British Journal of Ophthalmology 75:42-44 (1991).
Raj et al., "Objective autorefraction in posterior chamber pseudophakia," British Journal of Ophthalmology 74:731-733 (1990).

(56) References Cited

OTHER PUBLICATIONS

Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).

Retzlaff J., "A new intraocular lens calculation formula", J Am Intraocul Implant Soc. Apr. 1980 6(2):148-52. (Abstract).

Rosales et al., "Phakometry and lens tilt and decentration using a custom-developed Purkinje imaging apparatus: validation and measurements," Journal of the Optical Society of America, vol. 23, No. 3, Mar. 2006, pp. 509-520.

Rubin A., et al., "Refractive variation during autorefraction: multivariate distribution of refractive status", Optom Vis Sci. Jun. 1995;72(6):403-10 (Abstract).

Rubin A., et al., "Variation during autorefraction: influence of two different target types", Ophthalmic Physiol Opt. Jan. 1997;17(1):38-43 (Abstract).

Sanders et al., "Comparison of the SRK/T formula and other theoretical and regression formulas," J Cataract Refract Surg. 16:341-346 (May 1990).

Sanders et al., "Comparisons of the SRK™ formula and other second generation formulas," J Cataract Refract Surg 14;136-141 (Mar. 1988).

Senjo, et al., "Prediction of Postoperative Refraction Using Intraoperative Retinoscopy," Journal of Japanese Ophthalmological Society, 1999, vol. 103, No. 7, pp. 551-555, Abstract.

Siahmed K., et al., "Optic biometry in intraocular lense calculation for cataract surgery. Comparison with usual methods", J Fr Ophtalmol. Nov. 2001;24(9):922-6 (Abstract).

Siganos et al., "Autorefractometry after laser in situ keratomileusis," J Cataract Refract Surg 29:133-137 (Jan. 2003).

Supplemental Amendment filed Apr. 1, 2010 in U.S. Appl. No. 11/110,968, filed Apr. 20, 2005.

Supplementary European Search Report for Application No. 05737636.0, Dated Mar. 19, 2009.

Steele, G., et al., "Cycloplegic auto refraction results in pre-school children using the Nikon Retinomax Plus and the Welch Allyn SureSight", Optom Vis Sci. Aug. 2003;80(8):573-7 (Abstract).

Straub et al., "*Design of a compact Shack-Hartmann aberrometr for real-time measurement of aberrations in human eyes,*" 2000 Optical Society of America, pp. 110-113.

Suto et al., "Adjusting intraocular lens power for sulcus fixation," J Cataract Refract Surg 29:1913-1917 (Oct. 2003).

Tabernero et al., "Instrument for measuring the misalignments of ocular surfaces," Optical Society of America, Oct. 30, 2006, vol. 14, No. 22.

Thall et al., "Linear Regression Software for Intraocular Lens Implant Power Calculation," American Journal of Ophthalmology 101:597-599 (May 1986).

Thijssen JM., "The emmetropic and the iseikonic implant lens: computer calculation of the' refractive power and its accuracy", Ophthalmologica. 1975;171 (6):467-86 (Abstract).

Thompson et al., "A New Posterior Chamber Intraocular Lens Formula for Axial Myopes," Ophthalmology 91(5): 484-488 (May 1984).

Tromans et al., "Accuracy of intraocular lens power calculation in paediatric cataract surgery," Br J Ophthalmol 85:939-941 (2001).

Tseng, et al., "Calculating the optimal rotation of a misaligned toric intraocular lens," J Catactact Refract Surg, Laboratory Science, Oct. 2008, vol. 34, pp. 1767-1772.

Uozato et al., "Intraoperative Confirmation Device for IOL Centering," Folia Ophthalmologica Japonica, vol. 41, 1990, pp. 1325-1329.

Villada Jr., et al., "Comparative evaluation of the Allergan Humphrey 570 and Canon RK-I autorefractors: II, Objective autorefraction in pseudophakes", Eye. 1992;6 (Pt 3):287-9 (Abstract).

Walline JJ, "Repeatability and validity of astigmatism measurements", J Refract Surg. Jan.-Feb. 1999; 15(1):23-31 (Abstract).

Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.

Wood IC., "A review of autorefractors", Eye. 1987;1 (Pt 4):529-35 (Abstract).

Yalvac IS, et al., "Calculation of intraocular lens power with the SRK IIformula for axial high myopia" Eur J Ophthalmol. Oct.-Dec. 1996;6(4):375-8 (Abstract).

Zaldivar et al., "Intraocular lens power calculations in patients with extreme myopia," J Cataract Refract Surg 26:668-674 (May 2000).

DETERMINATION OF THE EFFECTIVE LENS POSITION OF AN INTRAOCULAR LENS USING APHAKIC REFRACTIVE POWER

This application is a continuation of U.S. patent application Ser. No. 12/835,668, filed Jul. 13, 2010, and entitled "DETERMINATION OF THE EFFECTIVE LENS POSITION OF AN INTRAOCULAR LENS USING APHAKIC REFRACTIVE POWER," which claims priority to U.S. Provisional Patent Application 61/225,532, filed Jul. 14, 2009, and entitled "DETERMINATION OF THE EFFECTIVE LENS POSITION OF AN INTRAOCULAR LENS USING APHAKIC REFRACTIVE POWER," both of which are hereby incorporated by reference herein in their entirety.

BACKGROUND OF THE INVENTION

Field of the Invention

The field of the invention relates to ophthalmic systems and procedures. In particular, the field of the invention relates to the determination of the post-surgical effective lens position (ELP) of an intraocular lens (IOL) and IOL power.

Description of the Related Art

Cataracts are clouded regions that can develop in the natural crystalline lens of an eye. A cataract can range in degree from slight clouding to complete opacity. Typically, formation of cataracts in human eyes is an age-related process. If left untreated, cataracts can lead to blindness. Surgeries have been developed for the treatment of cataracts by replacement of the natural crystalline lens with an artificial lens. Typically, an incision is made in the eye and the natural crystalline lens is removed. An artificial implant called an intraocular lens (IOL) is then inserted, for example, in the capsular bag of the eye in place of the natural crystalline lens. The spherical and/or astigmatic optical refractive power of the IOL may be selected so as to give the eye a desired amount of post-surgical refractive power. For example, the power of the IOL may be selected so as to place the eye in a substantially emmetropic state when combined with the refractive power of the cornea of the eye.

SUMMARY OF THE INVENTION

In some embodiments, a method for determining the optical power of an intraocular lens to be inserted into the eye of a patient comprises: receiving as an input an indication of the aphakic refractive power of the patient's eye; determining, with a processor, an estimate of the post-surgical effective lens position (ELP) of the intraocular lens for the patient's eye, the estimate being based on the indication of the aphakic refractive power of the patient's eye and on a relationship between aphakic refractive power and post-surgical intraocular lens ELP; and determining an amount of optical power for the intraocular lens to be inserted into the patient's eye based on the estimate of the post-surgical ELP of the intraocular lens in the patient's eye.

In some embodiments, a computer-readable medium comprises instructions that, when read by a computer, cause the computer to perform a method comprising: receiving as an input an indication of the aphakic refractive power of the patient's eye; determining an estimate of the post-surgical effective lens position (ELP) of the intraocular lens based on the indication of the aphakic refractive power of the patient's eye and on a relationship between aphakic refractive power and intraocular lens ELP; and determining an amount of optical power for the intraocular lens to be inserted into the eye of the patient based on the estimate of the post-surgical ELP of the intraocular lens.

In some embodiments, an ophthalmic method for determining a relationship between post-surgical effective lens position (ELP) of an intraocular lens and aphakic ocular power comprises: obtaining a plurality of indications of the aphakic power of a respective plurality of eyes; determining a plurality of indications of the post-surgical ELP of an intraocular lens for the respective plurality of eyes; and determining a relationship between the plurality of indications of the aphakic power and the plurality of indications of the post-surgical ELP using a processor.

In some embodiments, an ophthalmic instrument comprises: a measurement device for measuring the aphakic power of a patient's eye; and a processor for performing a method comprising, receiving an indication of the aphakic refractive power of the patient's eye from the measurement device, determining an estimate of the post-surgical effective lens position (ELP) of an intraocular lens to be inserted in the patient's eye, the estimate of the post-surgical ELP of the intraocular lens being based on the indication of the aphakic refractive power of the patient's eye and on a relationship between aphakic refractive power and intraocular lens ELP, and determining an appropriate amount of optical power for the intraocular lens to be inserted into the patient's eye based on the estimate of the post-surgical ELP of the intraocular lens.

BRIEF DESCRIPTION OF THE DRAWINGS

For purposes of summarizing the disclosure, certain aspects, advantages and features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein. Certain embodiments are illustrated in the accompanying drawings, which are for illustrative purposes only.

DETAILED DESCRIPTION OF THE PREFERRED EMBODIMENT

Figure 1:
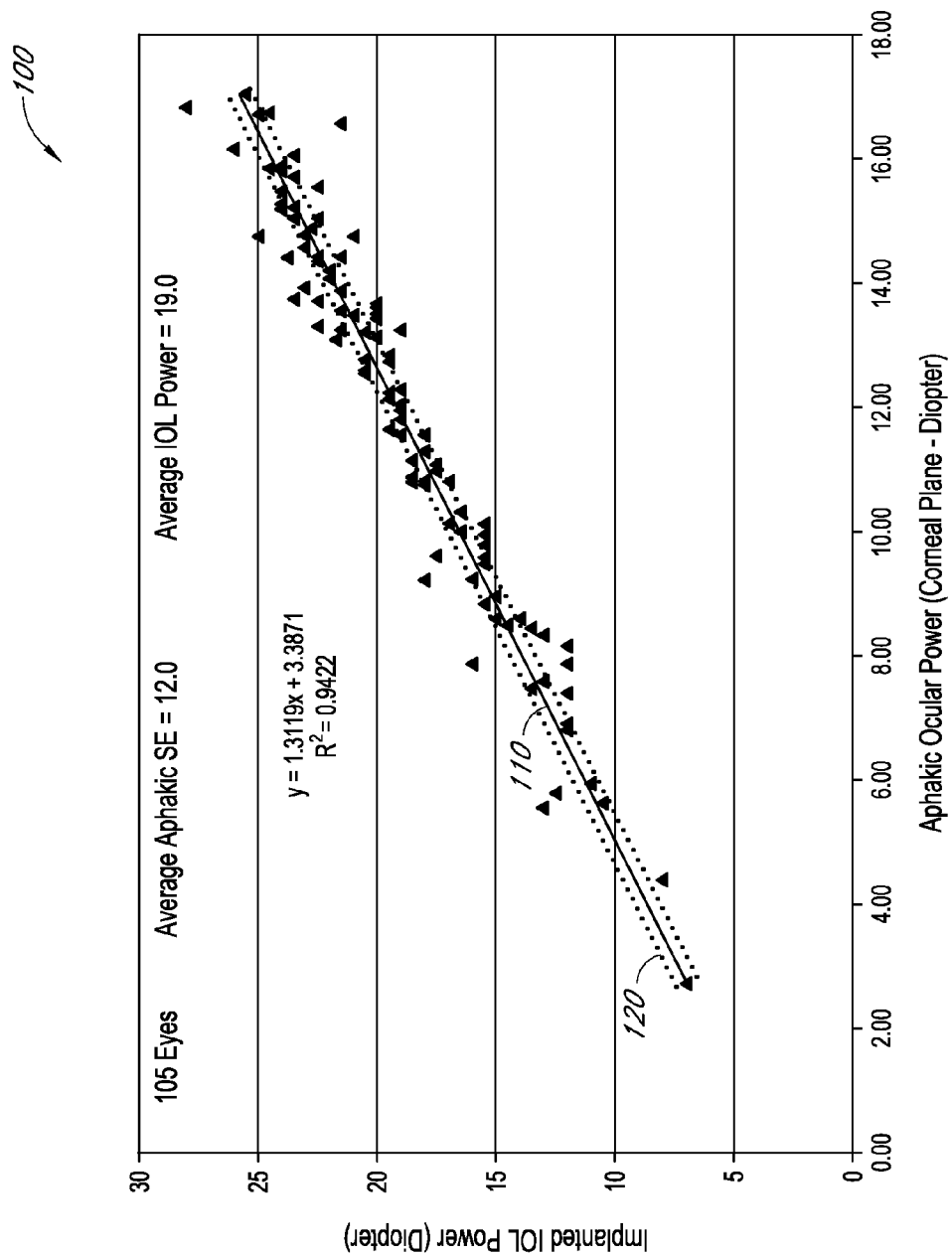
FIG. 1 is a plot of implanted IOL power versus aphakic ocular power for a sample group of eyes that underwent cataract surgery.

In a typical cataract surgery, a surgeon removes the natural crystalline lens from a patient's eye and an intraocular lens (IOL) is implanted in its place. By selecting an IOL having an appropriate amount of spherical and/or cylindrical power, an eye that prior to the surgery was, for example, myopic (near sighted), hyperopic (far sighted), and/or astigmatic can be restored to, for example, an emmetropic condition. The determination of an appropriate amount of IOL optical power for a given application is a significant aspect of obtaining satisfactory surgical outcomes for patients. Various factors can be considered when calculating the appropriate power for the IOL, such as 1) the axial length of the eye, for example, measured from the cornea to the retina; 2) the total optical power of the cornea, including its anterior and posterior surfaces; 3) the desired postoperative optical power (e.g., 0.0 diopters (D) of defocus for an emmetropic eye); and 4) the effective lens position (ELP) of the IOL, which can be understood, for example, as the distance from the corneal surface to the post-operative position of the IOL (e.g., the distance from corneal apex to the center of the IOL in its settled position).

Preoperative biometry measurements can be used to measure the axial length of the eye and the curvature of the anterior surface of the cornea. The axial length of the eye can be measured, for example, by an ultrasound device or by Optical Coherence Tomography (OCT), while the curvature of the anterior surface of the cornea can be measured by, for example, a keratometer (e.g., K values measured in orthogonal meridians that pass through the corneal apex, or anatomical center, of the cornea and are expressed in terms of the radii of curvature or as the dioptric power of the cornea along these orthogonal meridians) or corneal topographer (simulated K values). The total optical power of the cornea can then be estimated from the corneal curvature K values.

The ELP of the IOL affects the total refractive power of the post-surgical eye because of the differing amount of vergence it imparts to light in the eye depending upon its spatial position between the cornea and the retina. For example, a 20 diopter IOL that is axially displaced from the predicted ELP by only 0.5 mm could result in a 1.0 diopter error in postoperative refraction.

The ELP of the IOL has traditionally been difficult to determine. The position of the natural crystalline lens in a patient's eye can be measured. However, since transformation of the young crystalline lens into a cataract occurs somewhat differently from patient to patient, measurement of the position of the crystalline lens (cataract) prior to surgery often does not lead to an accurate determination of the ELP. Therefore, other methods for estimating ELP have been developed.

Early on, a fixed value was used for all eyes as an estimate of ELP, and the resulting residual refractive error was treated with glasses or contact lenses. Later, estimates of ELP were developed based on biometry data, such as measurements of the axial length and corneal curvature of the patient's eye. The estimation of ELP can also be based on horizontal corneal diameter, anterior chamber depth, lens thickness, preoperative phakic ocular refraction, and patient age. There are mathematical formulas for estimating ELP based on these factors. Such formulas include, for example, the Holladay 1, SRK/T, Hoffer Q, Holladay 2, and Hagis formulas. These formulas are used to calculate IOL power. However, these formulas generally only differ in the specific method used for estimating ELP. Therefore these formulas may be referred to as IOL power calculation formulas or ELP estimation formulas.

The Holladay 1, SRK/T, and the Hoffer Q formulas are considered second-generation formulas. The Holladay 2 and the Hagis formulas are considered third-generation formulas. An article entitled "Accuracy of intraocular lens power prediction using the Hoffer Q, Holladay 1, Holladay 2, and SRK/T formulas," by Narvaez, et al., appeared in the December 2006 issue of the Journal of Cataract & Refractive Surgery. The article compared the effectiveness of these four IOL power formulas for a group of patients. The results presented below show that the three second-generation formulas are generally as effective as the Holladay 2, which uses more of the above-named variables.

|  |  | Mean Absolute Difference, Predicted Versus Actual Postoperative SE Refraction (D) ± SD | | | |
|---|---|---|---|---|---|
| Axial Length (mm) | Eyes | Holladay 1 | Holladay 2 | Hoffer Q | SRK/T |
| <22.0 | 14 | 0.85 ± 0.58 | 0.90 ± 0.67 | 0.72 ± 0.48 | 0.91 ± 0.58 |
| 22.0 to <24.50 | 236 | 0.57 ± 0.45 | 0.56 ± 0.44 | 0.58 ± 0.46 | 0.56 ± 0.45 |
| 24.5 to 26.00 | 72 | 0.50 ± 0.38 | 0.46 ± 0.36 | 0.51 ± 0.36 | 0.49 ± 0.38 |
| >26.00 | 16 | 0.78 ± 0.73 | 0.65 ± 0.76 | 0.75 ± 0.70 | 0.65 ± 0.83 |
| All eyes | 338 | 0.58 ± 0.46 | 0.56 ± 0.46 | 0.58 ± 0.46 | 0.57 ± 0.47 |

As the technology surrounding cataract surgeries continues to improve, increasingly, patients have expectations of being spectacle free after cataract surgery. In order to achieve emmetropic results for patients, there is a need to improve ELP estimation. Since the accuracy of the ELP estimation is dependent upon the accuracy of the biometry measurements which are input into the formula, the larger the number of measurement inputs that are used in the ELP estimation formula, the greater the opportunity for measurement inaccuracies to be introduced. There is potential for mistakes to occur in each biometry measurement that is made. Thus, it would be desirable to reduce the number of measurements needed as inputs for an ELP estimation formula.

In addition, the use of keratometry measurements in ELP estimation formulas may be problematic in the case of patients who have had previous refractive surgery (e.g., RK, PRK, LASIK, etc). Typically, the total power of the cornea is determined from keratometer readings of the front surface of the cornea based on a valid assumption regarding the relationship between the front surface of the cornea and the back surface of the cornea. To correct a person's ocular refractive error, various refractive surgery procedures change the shape of the front surface of the cornea. Thus, determining the total corneal power from the keratometer measurement may not be clinically valid for post refractive surgery patients. Numerous formulas have appeared in the ophthalmic literature purporting to most accurately estimate total corneal power based on keratometer readings for post refractive patients. However, the accuracy of these formulas for estimating total corneal power is not proven. Since refractive surgeries that alter the shape of the cornea have become relatively common, this problem affects a significant number of cataract patients. Thus, it would be beneficial to reduce or eliminate the dependence of ELP estimates on keratometric measurements.

Systems and methods are described herein, which, in some embodiments, eliminate the need for total corneal power and axial length measurements. Instead, total corneal power and axial length are replaced by an indication of aphakic ocular power. In some embodiments, an ELP estimation formula is provided that does not receive total corneal power and axial length measurements as inputs but instead receives an indication of aphakic ocular power. In some embodiments, the indication of aphakic ocular power is an intraoperative direct measurement of the aphakic ocular power of the patient's eye.

In some embodiments, the direct measurement of aphakic ocular power is made using a wavefront aberrometer (e.g., Talbot-Moiré, Shack-Hartmann, or others), though other instruments can also be used. The wavefront aberrometer may be mounted to, and optically aligned with, a surgical microscope used by the surgeon to perform the cataract surgery. Such a device is described in US Patent Publication 2005/024327, which corresponds to co-pending U.S. patent application Ser. No. 11/110,653, filed Apr. 20, 2005 and entitled "INTEGRATED SURGICAL MICROSCOPE AND WAVEFRONT SENSOR." One type of wavefront aberrometer that is suitable for performing the types of intraoperative measurements described herein is a Talbot-Moiré wavefront aberrometer such as the one described in U.S. Pat. No. 6,736,510, issued May 18, 2004 and entitled "OPHTHALMIC TALBOT-MOIRÉ WAVEFRONT SENSOR." The foregoing references are both hereby incorporated by reference in their entirety.

Briefly, the Talbot-moiré wavefront aberrometer functions by introducing a probe laser beam into the patient's eye. The probe laser beam can be aligned to be coincident with the visual axis of the patient's eye, for example. The probe laser beam passes through the cornea, including the anterior and posterior surfaces, and is incident upon the retina. The probe beam scatters from the retina, for example, in such a way as to behave as a point source of light at the retina. The scattered probe beam light passes back through the eye, including the cornea. The optical wavefronts of the probe beam are altered according to the refractive properties of the eye (e.g., according to the shapes of the anterior and posterior surfaces of the cornea). The altered wavefront can then be analyzed to determine the optical power of the eye, including, for example, spherical power, astigmatic power, and astigmatic axis.

The aphakic ocular power of a patient's eye is dependent upon the total corneal power and the axial length of the patient's eye. In fact, a theoretical aphakic ocular power value can be calculated from corneal power and axial length data. However, in some embodiments, it is advantageous to instead measure aphakic ocular power directly and to use this measurement to estimate the ELP of the IOL for several reasons. First, a direct measurement of aphakic ocular power is not dependent upon a formula for estimating total corneal power from the curvature of its anterior surface. As discussed herein, the accuracy of such an estimate suffers in the case of patients who have had prior refractive surgery. Instead, the aphakic ocular power measurement actually measures and accounts for the optical power contribution of both the anterior surface and the posterior surface of the cornea even in cases where the anterior surface has been altered in a separate refractive surgery; it does not rely upon a modeled relationship between the respective shapes of the two corneal surfaces.

Second, since the aphakic ocular power measurement can be made through the pupil, for example, with respect to the visual axis of the patient's eye, rather than the optical axis, then the contribution of total corneal power to the aphakic ocular power measurement corresponds to the optical power that the patient actually experiences through the eye. In cases where, for example, the pupil is not centered on the anatomical center of the cornea, the corneal power measured with respect to the visual axis of the eye can be different than the corneal power measured with respect to the anatomical center of the cornea, as may be done with a keratometer.

Third, the ability to replace the corneal power and axial length measurements with a single measurement of aphakic ocular power reduces the number of measurements that need to be made to provide input data for the estimation of ELP. This in turn reduces opportunity for error to be introduced in the measurements. It may also reduce the amount of time for pre-operative diagnostics.

In some embodiments, a cataract surgery is performed by removing the natural crystalline lens from the patient's eye. In some embodiments, preoperative biometry measurements of the corneal curvature and axial length are not required. Instead, a surgeon measures the aphakic ocular power of the patient's eye during the surgery once the natural crystalline lens has been removed. As discussed herein, the aphakic ocular power can be effectively substituted for measurement data relating to the corneal power and axial length of the patient's eye since aphakic ocular power depends upon these two characteristics of the eye.

Once the aphakic ocular power of the eye (e.g., spherical power, cylindrical power, spherical equivalent power, etc.) has been obtained, it can be used to determine an estimate of the ELP of the IOL. The estimated ELP can then be used to determine IOL power using a refractive IOL power formula that is a function of, for example, aphakic spherical equivalent power (SE=sphere value+½ the cylinder value) and of the ELP estimate. The IOL power formula may also be a function of K measurements, though the ultimate dependence of IOL power on K measurements is reduced due to the reduced dependence of the ELP estimate on K measurements.

IOL power can be calculated, for example, according to the following formula, where "Desired_PostRx" is the desired post-operative refraction and the "V" in each term is the vertex distance (e.g., 0 mm for "Aphakic_SE" and 13 mm for "Desired_PostRx"):

$$IOLPower = \frac{1336}{\frac{1336}{\frac{1000}{\frac{1000}{Aphakic\_SE} - V} + K} - ELP} - \frac{1336}{\frac{1336}{\frac{1000}{\frac{1000}{Desired\_PostRx} - V} + K} - ELP}$$

Once the IOL power has been determined, the surgeon can select an appropriate IOL, implant it in the capsular bag, and complete the surgery.

In some embodiments, as described herein, ELP is estimated from aphakic ocular power, for example without using direct measurements of corneal power and axial length. This can be done by receiving as an input an indication of the aphakic refractive power of the patient's eye. The indication of aphakic refractive power of the patient's eye can be, for example, a direct intraoperative measurement of the aphakic ocular power. Such a measurement can be obtained using, for example, the wavefront aberrometer described herein. Then, an estimate of the post-surgical effective lens position (ELP) of the intraocular lens for the patient's eye can be determined using, for example, processing electronics.

The estimate of ELP can be calculated from aphakic power based on a relationship (e.g., a mathematical function) between aphakic refractive power and post-surgical intraocular lens ELP. For example, the relationship between aphakic refractive power and post-surgical intraocular lens ELP may be expressed mathematically where ELP is written as a function of aphakic ocular power. Finally, the appropriate optical power for the intraocular lens to be inserted into the patient's eye can be determined based on the estimate of the post-surgical ELP of the intraocular lens in the patient's eye. The estimated ELP and/or the IOL power can then be output to the surgeon to be used in the selection of a suitable IOL for the patient's eye.

As just described, determining IOL power from aphakic ocular power may involve estimating ELP based on aphakic ocular power and, in some embodiments, not based on measurements of corneal curvature and axial length. In some embodiments, determining a relationship between ELP and aphakic ocular power can be accomplished by obtaining indications of the aphakic power of a plurality of eyes. For example, the plurality of eyes can be a statistically significant sample size of eyes upon which cataract surgeries have been performed. In some embodiments, the indications of aphakic refractive power for the plurality of eyes are direct intraoperative measurements of the aphakic ocular power of the eyes. In some embodiments, the indications of aphakic ocular power for the plurality of eyes are calculated values of theoretical aphakic ocular power determined from corneal power and axial length data.

Next, indications of the post-surgical ELP of an intraocular lens in the plurality of eyes can be determined. This can be done, for example, by measuring post-surgical ELP of the IOL in the sample group of eyes using ultrasound or optical coherence tomography. Alternatively, or additionally, the indications of post-surgical ELP can be ELP estimates calculated using ELP estimation formulas, such as those described herein (e.g., the Holladay 1, Holladay 2, Hoffer Q, or SRK/T formulas). Finally, a processor can be used to correlate the indications of the aphakic ocular power of the eyes with the respective indications of the post-surgical ELP. The processor can also be used to determine a mathematical function that adequately describes the relationship between aphakic ocular values and the ELP values. The mathematical relationship can relate, for example, ELP as a function of aphakic ocular power. This function can then be used to determine an estimate of the ELP of an IOL for a patient's eye that is outside of the sample set.

These and other methods are illustrated with respect to FIGS. 1-8, which will now be described in detail. Unless otherwise noted, the data described herein and with respect to FIGS. 1-8 is based on a particular IOL intended to be inserted in the capsular bag of an eye. However, the systems and methods described herein are applicable to any type of IOL. In addition, the systems and methods described herein are applicable to IOLs intended to be inserted at other locations in the eye (e.g., the anterior chamber or the sulcus).

FIG. 1 is a plot 100 of implanted IOL power versus aphakic ocular power for a sample group of eyes that underwent cataract surgery. The implanted IOL power values are plotted on the axes as a function of aphakic ocular power, and are indicated on the plot 100 as triangles. While in some embodiments the measure of aphakic ocular power is the spherical equivalent power of the aphakic eye, in other embodiments the measure of aphakic ocular power can be the spherical power, the cylindrical power, or some other combination of the two (other than spherical equivalent power).

In this case (and in FIGS. 2-6 and 8), the aphakic ocular power values are theoretical aphakic spherical equivalent values calculated from corneal power and axial length data for each of the eyes. However, actual direct aphakic ocular power measurements obtained intraoperatively for each of the eyes could have been used instead.

In this particular sample set of eyes, the aphakic ocular power values range from approximately 2.5 diopters to approximately 17 diopters. Each of the plotted aphakic ocular power values corresponds to one of 105 eyes that made up the sample set. Each aphakic ocular power value (shown as the amount of power needed to correct the aphakic eye) is plotted versus the implanted IOL power that was selected in the cataract surgery for the corresponding eye. The aphakic ocular power data and the implanted IOL power data were analyzed with regression techniques to determine a fitted line 110. The fitted line 110 shows the empirical relationship between the aphakic ocular power data and the implanted IOL power data. Thus, the equation of the line 110 can be used to determine the power of an IOL to be inserted into an eye having a specified aphakic ocular power, or vice versa. The line 110 is of the form y=ax+b, where a and b are constants. In the equation, y corresponds to the implanted IOL power and it is written as a function of x, which corresponds to the aphakic ocular power. For the particular IOL type, measurement units, and sample set of eyes that were used, the equation of the fitted line was found to be y=1.3119x+3.3871, though the constants a and b will vary depending, for example, on these factors.

As indicated on the plot 100, there is a relatively good correlation between the aphakic ocular power and the implanted IOL power ($R^2$=0.9422), thus indicating that aphakic ocular power is a relatively good explanatory variable for implanted IOL power. However, FIG. 1 also shows a dotted box 120 around the fitted line 110. The dotted box 120 shows the range of implanted IOL power values that are within ±0.5 diopters of the value predicted by the equation for the fitted line 110. As illustrated, a relatively large percentage of the implanted IOL power values lies outside of this ±0.5 diopter range, meaning that if the implanted IOL power value had actually been selected based on the illustrated mathematical relationship (i.e., the fitted line 110), the surgery would have resulted in a possible residual refractive error of greater than 0.5 diopters.

The error between the IOL power values predicted based upon aphakic ocular power (i.e., the line 110) and those IOL power values that were actually used (i.e., the plotted triangles) is attributable, at least in part, to the fact that the illustrated relationship does not account for the ELP of the IOLs. As discussed herein, the ELP of the IOL has a clinically significant effect on the refractive power of the pseudophakic eye after the IOL has been inserted. Therefore, in some embodiments, it would be desirable to determine a relationship between aphakic ocular power and ELP. In some embodiments, such a relationship could be used to improve the accuracy of IOL power values calculated based on aphakic ocular power values, as indicated in FIG. 1.

Figure 2:
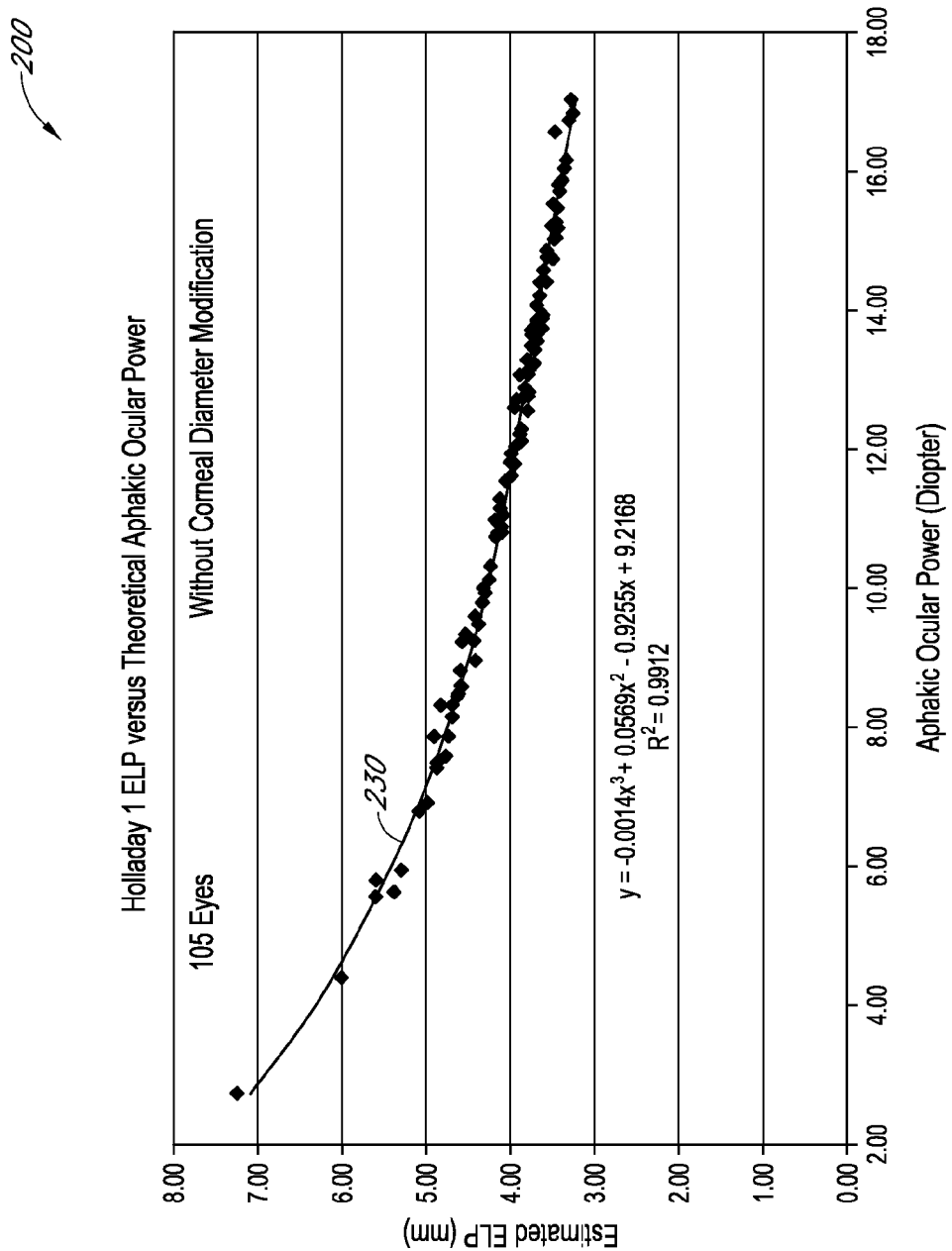
FIG. 2 is a plot of estimated ELP versus aphakic ocular power for the sample group of eyes, the estimated ELP having been determined using the Holladay 1 formula.

FIG. 2 is a plot 200 of estimated ELP versus aphakic ocular power for the sample group of eyes, the estimated ELP having been determined using the Holladay 1 formula. The estimated ELP values are plotted on the axes as a function of aphakic ocular power. These values are indicated as diamonds on the plot 200. In some embodiments, the aphakic ocular power values are the spherical equivalent optical power of the aphakic eyes. In other embodiments, the aphakic ocular power values can be the spherical aphakic optical power, the cylindrical aphakic optical power, or some other combination of the two.

The aphakic ocular power values can be actual directly-measured aphakic ocular power values obtained from the eyes intraoperatively. In such cases, it is advantageous for the aphakic ocular power values of the sample eyes to span the meaningful range of aphakic ocular power values in the population in a statistically-meaningful way.

Alternatively, as was the case here, theoretical aphakic ocular power values calculated from corneal power and axial length data for the eyes are also useful for determining a relationship between aphakic ocular power and ELP (e.g., estimated ELP). In such cases, it may be advantageous for both the corneal power and axial length data of the sample eyes to span the respective meaningful ranges of these values found in the population in a statistically-meaningful way. In some embodiments, if the relationship between aphakic ocular power and estimated ELP is determined using calculated theoretical aphakic ocular power values, it can be later modified, improved, or refined based on actual aphakic ocular power measurements using, for example regression analysis.

The estimated ELP values illustrated in FIG. 2 were calculated from the corneal power and axial length data for the eyes using the Holladay 1 formula, though, as described herein, other formulas can also be used. In addition, actual measured ELP values obtained postoperatively (e.g., by ultrasound or OCT) could also have been used in order to establish the relationship between aphakic ocular power and ELP (e.g., measured ELP).

The aphakic ocular power data and the estimated ELP data were correlated in order to determine a mathematical relationship between the two sets of data. In particular, least squares regression techniques were used to identify a fitted curve 230 that adequately describes the relationship between the two sets of data. However, many different techniques for determining relationships between the aphakic ocular power and estimated ELP data, and/or for calculating estimated ELP values from aphakic ocular power values, can be used, including various types of regression analysis, curve fitting techniques, neural networks, fuzzy logic, lookup tables, etc.

In some embodiments, the curve 230 is a cubic polynomial, as indicated in FIG. 2, though other degrees of polynomials or types of functions can also be used. The curve 230 generally slopes downward from left to right, indicating that eyes with relatively high aphakic ocular power are estimated to have shorter effective lens positions than eyes with relatively low amounts of aphakic ocular power. The fitted curve 230 shows the empirical relationship between the aphakic ocular power data and the estimated ELP values for each of the eyes. Thus, the equation of the curve 230 can be used to determine an estimated ELP value for an IOL implanted into an eye having a specified aphakic ocular power. The equation of the curve 230 is of the form $y=ax^3+bx^2+cx+d$, where a, b, c, and d are constants. In the equation, y corresponds to the estimated ELP value for the eye and it is written as a function of x, which corresponds to the aphakic ocular power of the eye.

For the particular IOL type, measurement units, and sample set of eyes that were used, the equation of the fitted curve 230 was found to be $y=-0.0014x^3+0.0569x^2-0.9255x+9.2168$, though the constants a, b, c, and d will vary depending, for example, on these factors. In some embodiments, the relationship between aphakic ocular power and estimated ELP using the Holladay 1 formula can be described by a line, a quadratic polynomial, or a higher-order polynomial.

As indicated on the plot 200, there is a strong correlation between the aphakic ocular power and the estimated ELP values ($R^2=0.9912$), thus indicating that aphakic ocular power is a good explanatory variable for estimated ELP. The relatively high degree of correlation between these values is an advantageous result. While certain ELP formulas (including the Holladay 1 formula) have been verified to demonstrate a meaningful relationship between ELP on the one hand and corneal power and axial length on the other hand, and while aphakic ocular power likewise depends on corneal power and axial length, it does not necessarily mathematically follow that there is a well-defined, meaningful relationship between ELP and aphakic ocular power. Nevertheless, FIG. 2 illustrates that such a relationship does in fact exist.

One feature, for example, of such a well-defined relationship is that a mathematical function (e.g., a line or higher-order polynomial curve, etc.) can be found to relate ELP and aphakic ocular power values with an adequate degree of correlation (e.g., a minimum $R^2$ value over representative ranges of ELP, for example measured in millimeters, and aphakic ocular power, for example measured in diopters). For example, in some embodiments, the $R^2$ value is at least 0.925. In some embodiments, the $R^2$ value is at least 0.950. In some embodiments, the $R^2$ value is at least 0.975. In some embodiments, the $R^2$ value is at least 0.990.

The existence of a well-defined, meaningful relationship between aphakic ocular power and validated estimates of ELP (e.g., those calculated using formulas such as the Holladay 1, Holladay 2, Hoffer Q, and SRK/T formulas, etc.) allows for IOL power to be calculated from aphakic refractive power without relying on corneal power (e.g., corneal Ks) and/or axial length measurements but while still maintaining the advantages associated with using a validated ELP estimate in the IOL power calculation.

Certain formulas for estimating ELP (including the Holladay 1 ) may employ correction modifiers which place certain limits on the magnitude of the ELP estimate or otherwise modify it. For example, certain ELP estimation formulas include correction modifiers to limit the estimated ELP for relatively long eyes due to physiological reasons (e.g., the ELP not being expected to be greater than 7 mm behind the cornea). For long eyes the ELP may not be as large as a linear relationship between axial length of a particular eye compared to that of the average eye may indicate. The degree to which the ELP is modified may depend on the overall size of the eye, which can be indicated by the corneal diameter, sometimes referred to as the white-to-white distance. This parameter can be used, for example in conjunction with aphakic ocular power, to determine or modify an estimate of ELP. This can be done, for example, by regression analysis. Other ocular characteristics can also be used, for example in conjunction with aphakic ocular power, to determine or modify an estimate of ELP.

Figure 3:
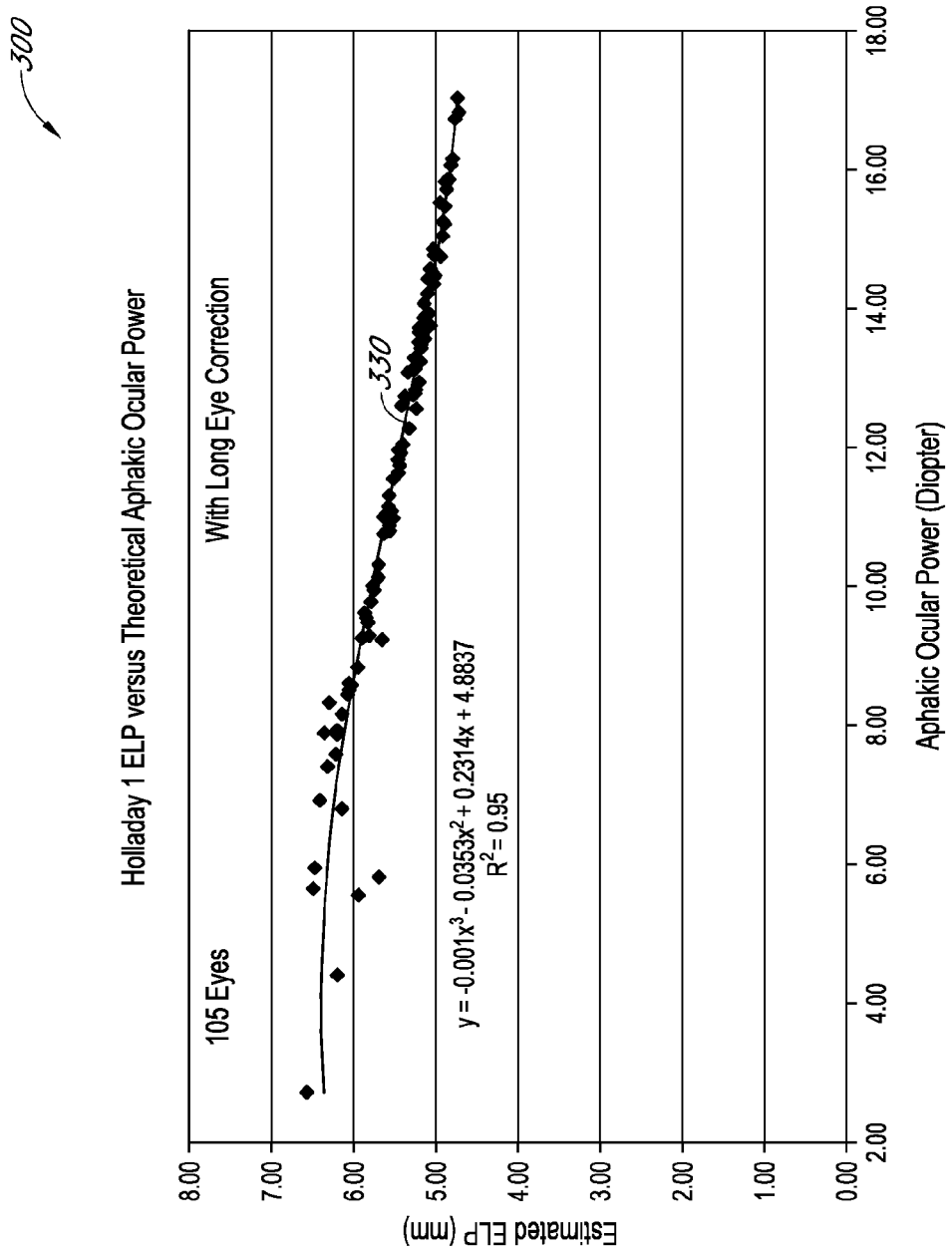
FIG. 3 is a plot of estimated ELP versus aphakic ocular power for the sample group of eyes, the estimated ELP having been determined using the Holladay 1 formula and corrected to reduce errors attributable to relatively long axial length.

FIG. 3 is a plot 300 of estimated ELP versus aphakic ocular power for the sample group of eyes, the estimated ELP having been determined using the Holladay 1 formula and corrected to reduce errors attributable to relatively long axial length. As in FIG. 2, the estimated ELP values are plotted on the axes as a function of spherical equivalent aphakic ocular power. The aphakic ocular power values and estimated ELP values for the sample set of eyes can be obtained similarly as described with respect to FIG. 2. In addition, the aphakic ocular power values and estimated ELP values can be correlated using techniques similar to those described with respect to FIG. 2.

In FIG. 3, the aphakic ocular power data and the estimated ELP data were correlated in order to determine a mathematical relationship between the two sets of data. In particular, least squares regression techniques were used to identify a fitted curve 330. In some embodiments, the curve 330 is a cubic polynomial, as indicated in FIG. 3, though other degrees of polynomials or types of functions can also be used. The curve 330 shows that the long eye correction disproportionately affected the estimated ELP values for eyes with relatively strong aphakic ocular power (the ELP estimates for the highest powered aphakic eyes increased from about 3.25 mm in FIG. 2 to about 4.75 mm in FIG. 3) as compared to the eyes with weaker aphakic ocular power (the ELP estimates for the lowest powered aphakic eye decreased from about 7.25 mm in FIG. 2 to about 6.5 mm in FIG. 3). As noted, the overall effect of the long eye correction was to increase ELP estimates for higher-powered aphakic eyes and to decrease the ELP estimates for lower-powered aphakic eyes, thus compressing the estimated ELP values into a tighter range.

The fitted curve 330 shows the empirical relationship between the aphakic ocular power data and the long eye-corrected estimated ELP values for each of the eyes. Thus, the equation of the curve 330 can be used to determine a long eye-corrected estimated ELP value for an IOL implanted into an eye having a specified aphakic ocular power. The equation of the curve 330 in FIG. 3 is $y=-0.001x^3-0.0353x^2+0.2314x+4.8837$, though the constants a, b, c, and d will vary depending, for example, on measurement units, the sample data, IOL type, etc. In some embodiments, the relationship between aphakic ocular power and estimated ELP using the Holladay 1 formula is described by a line, a quadratic polynomial, or a higher-order polynomial.

As indicated on the plot 300, the correlation between the aphakic ocular power and the long eye-corrected estimated ELP values is slightly lower than the correlation between aphakic ocular power and the uncorrected estimated ELP values ($R^2=0.95$ versus $R^2=0.9912$). However, the correlation is still relatively strong, thus indicating that aphakic ocular power is a good explanatory variable for long eye-corrected estimated ELP.

Figure 4:
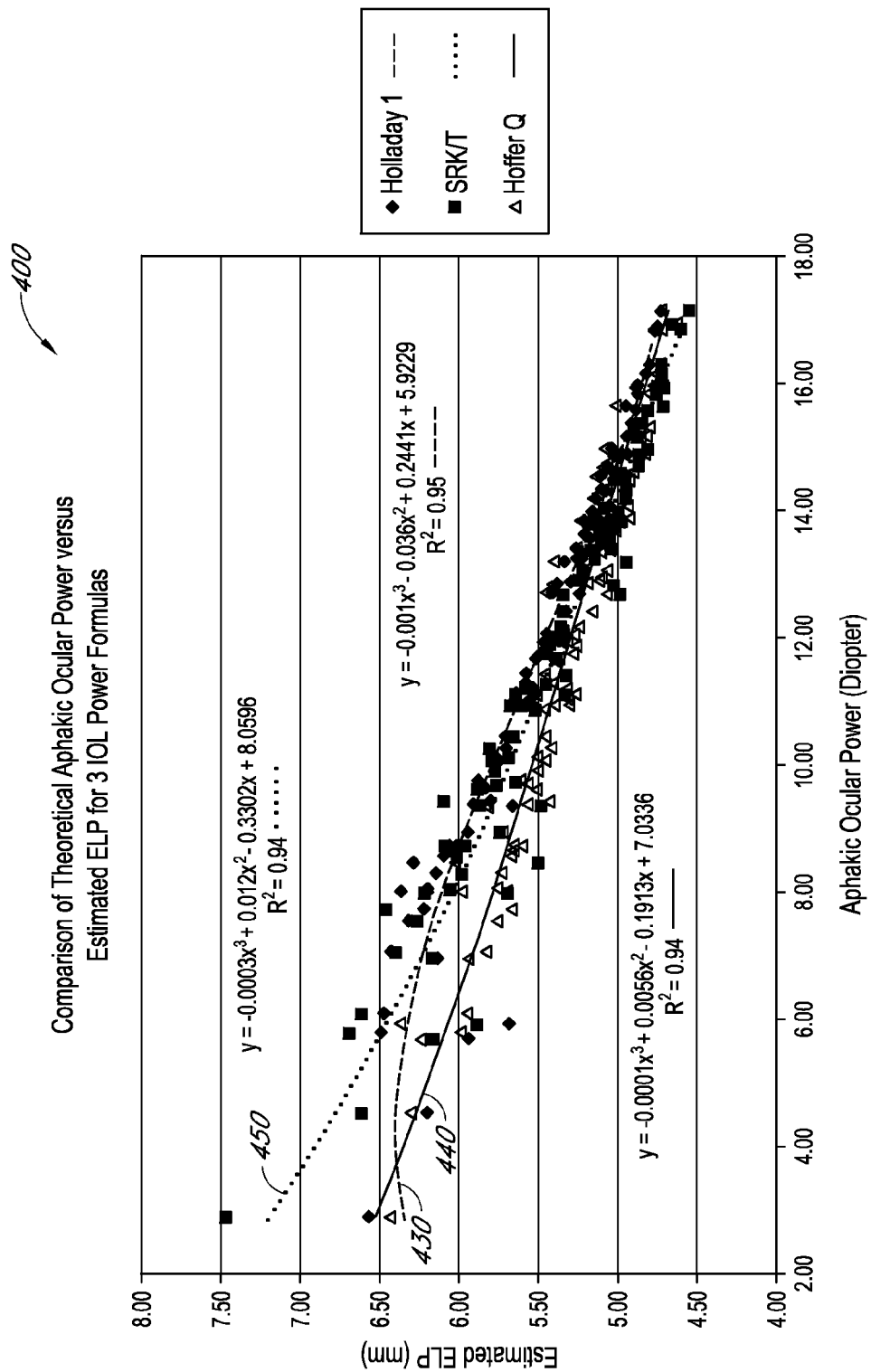
FIG. 4 is a plot of three different types of estimated ELP versus aphakic ocular power for the sample group of eyes, the three different types of estimated ELP being the Holladay 1 formula, the SRK/T formula, and the Hoffer Q formula.

FIG. 4 is a plot 400 of three different types of estimated ELP versus aphakic ocular power for the sample group of eyes, the three different types of estimated ELP being the Holladay 1 formula, the SRK/T formula, and the Hoffer Q formula. The ELP estimates in FIG. 4 are long eye-corrected, but this is not required. The aphakic ocular power data and the estimated ELP data can be collected and analyzed in ways similar to those described with respect to the preceding figures.

FIG. 4 shows a comparison of ELP estimates calculated using the Holladay 1, the SRK/T, and the Hoffer Q formulas. The Holladay 1 estimates are plotted as a function of aphakic ocular power and are represented on the plot 400 as diamonds. A fitted curve 430 for the Holladay 1 data is shown with a dashed line. The equation of the fitted curve 430 was found to be $y=-0.001x^3-0.036x^2+0.2441x+5.9229$, though the constants a, b, c, and d will vary, for example, depending on previously-mentioned factors. In some embodiments, the relationship between aphakic ocular power and estimated ELP using the Holladay 1 formula can be described by a line, a quadratic polynomial, or a higher-order polynomial. The correlation between aphakic ocular power and estimated ELP for the Holladay 1 estimates was relatively strong ($R^2=0.95$).

The SRK/T estimates are plotted as a function of aphakic ocular power and are represented on the plot 400 as squares. A fitted curve 450 for the SRK/T data is shown with a dotted line. The equation of the fitted curve 450 was found to be $y=-0.0003x^3+0.012x^2-0.33302x+8.0596$, though the constants a, b, c, and d will vary, for example, depending on previously-mentioned factors. In some embodiments, the relationship between aphakic ocular power and estimated ELP using the SRK/T formula can be described by a line, a quadratic polynomial, or a higher-order polynomial. The correlation between aphakic ocular power and estimated ELP for the SRK/T estimates was relatively strong ($R^2=0.94$).

The Hoffer Q estimates are plotted as a function of aphakic ocular power and are represented on the plot 400 as triangles. A fitted curve 440 for the Hoffer Q data is shown with a solid line. The equation of the fitted curve 440 was found to be $y=-0.0001x^3+0.0056x^2-0.1913x+7.0336$, though the constants a, b, c, and d will vary, for example, depending on previously-mentioned factors. In some embodiments, the relationship between aphakic ocular power and estimated ELP using the Hoffer Q formula can be described by a line, a quadratic polynomial, or a higher-order polynomial. The correlation between aphakic ocular power and estimated ELP for the Hoffer Q estimates was relatively strong ($R^2=0.94$).

As indicated in FIG. 4, the correlation between aphakic ocular power and estimated ELP was relatively strong for each of the three ELP formulas tested. Thus, while the results for the three formulas are different, aphakic ocular power is seen to be a good explanatory variable for ELP estimates calculated using the Holladay 1, the SRK/T, and the Hoffer Q formulas.

Figure 5:
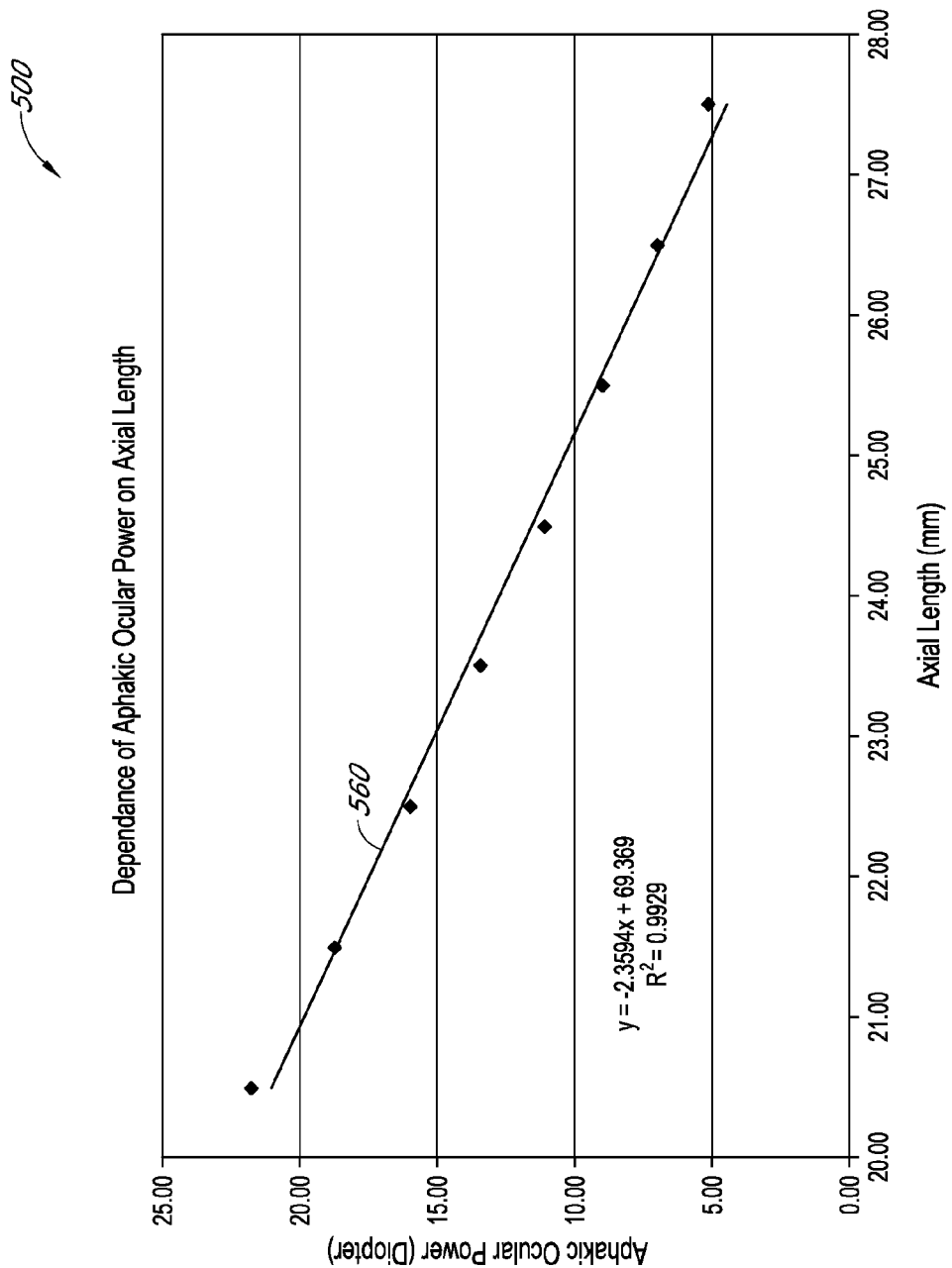
FIG. 5 is a plot of aphakic ocular power versus axial length.
Figure 6:
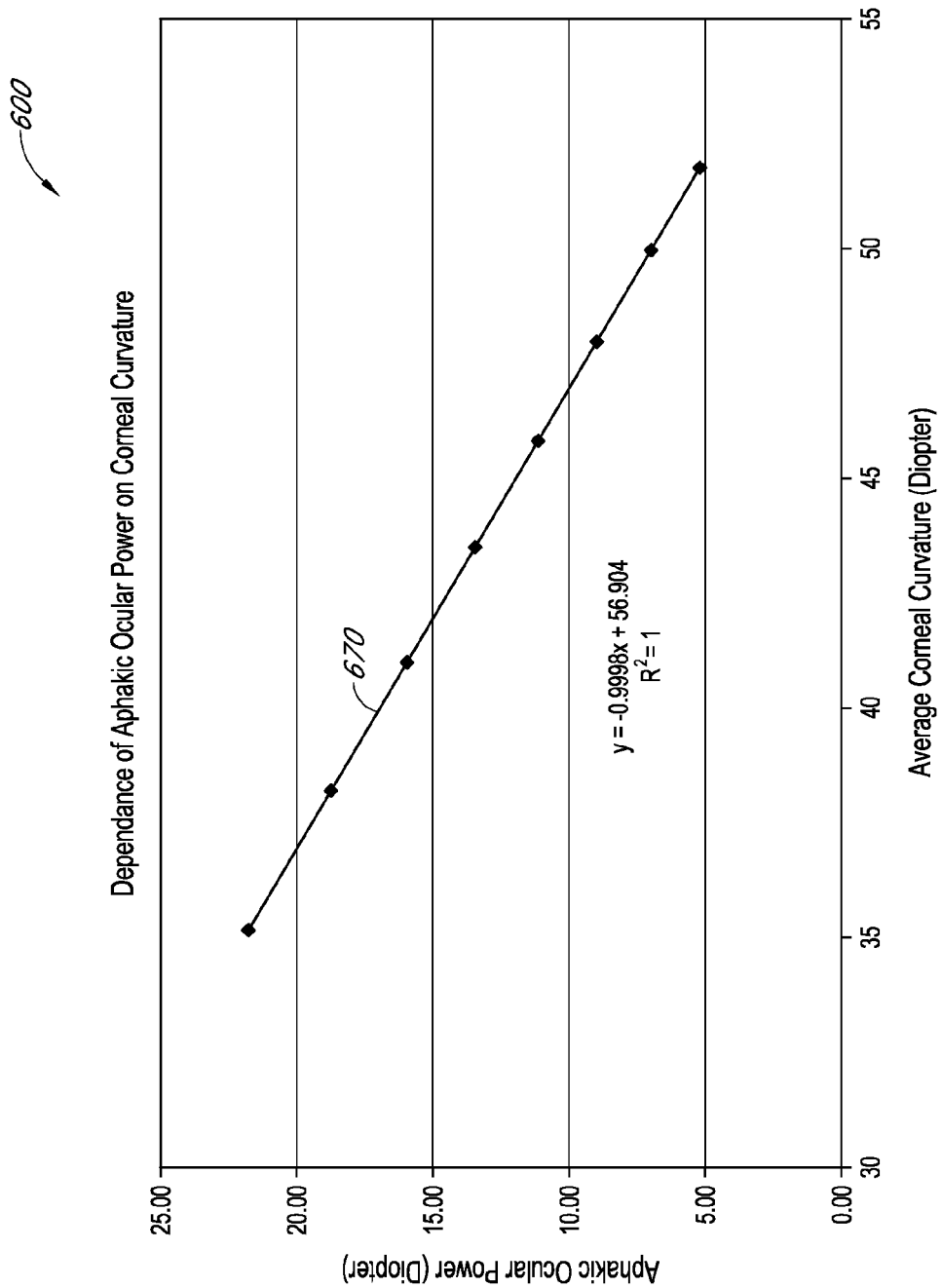
FIG. 6 is a plot of aphakic ocular power versus corneal curvature.

As discussed herein, aphakic ocular power is dependent upon corneal power and axial length. The dependencies of aphakic ocular power (e.g., spherical equivalent aphakic ocular power) on axial length and corneal curvature are illustrated in FIGS. 5 and 6, respectively. Axial length measurement values and corneal curvature measurement values (e.g., average corneal curvature) were obtained for a set of eyes. The axial length measurement values span the range from about 20.5 mm to about 27.5 mm. The corneal curvature values span the range from about 35 diopters to about 52 diopters. The axial length and corneal curvature measurement values were used to calculate theoretical aphakic ocular power values for each of the tested eyes.

FIG. 5 is a plot 500 of aphakic ocular power versus axial length. The aphakic ocular power values are plotted as a function of axial length, with a constant K value, and are indicated by the diamonds on the plot 500. A fitted line 560 was calculated using the techniques described herein. The fitted line 560 represents the mathematical relationship between axial length and aphakic ocular power. The equation of the line was found to be $y=-2.3594x+69.369$. As indicated in FIG. 5, the correlation between aphakic ocular power and axial length was very good over this range ($R^2=0.9929$), indicating that axial length is a very good predictor of aphakic ocular power.

FIG. 6 is a plot 600 of aphakic ocular power versus corneal curvature. The aphakic ocular power values are plotted as a function of corneal curvature (e.g., average corneal curvature), with a constant axial length, and are indicated by the diamonds on the plot 600. A fitted line 670 was calculated using the techniques described herein. The fitted line 670 represents the mathematical relationship between the corneal curvature and aphakic ocular power. The equation of the line was found to be $y=-0.9998x+56.904$. As indicated in FIG. 6, the correlation between aphakic ocular power and corneal curvature was essentially perfect over this range ($R^2=1$), indicating that corneal curvature is a very good predictor of aphakic ocular power.

With reference to FIGS. 5 and 6, the dependence of aphakic ocular power (e.g., spherical equivalent aphakic ocular power) on axial length was somewhat stronger than its dependence upon corneal curvature, as indicated by the greater magnitude slope of the fitted line 560 as compared to the fitted line 670. Thus, in some embodiments, it is advantageous to determine which of the various ELP estimation formulas exhibits the strongest correlation with axial length measurements. The selected ELP estimation formula can be used to determine the relationship between aphakic ocular power and ELP, as described herein. This relationship can then be used to determine an estimate of ELP for an IOL in a patient's eye given the intraoperatively-measured aphakic ocular power of the patient's eye. Finally, this estimate can be used in the calculation of IOL power, as described herein.

Figure 7:
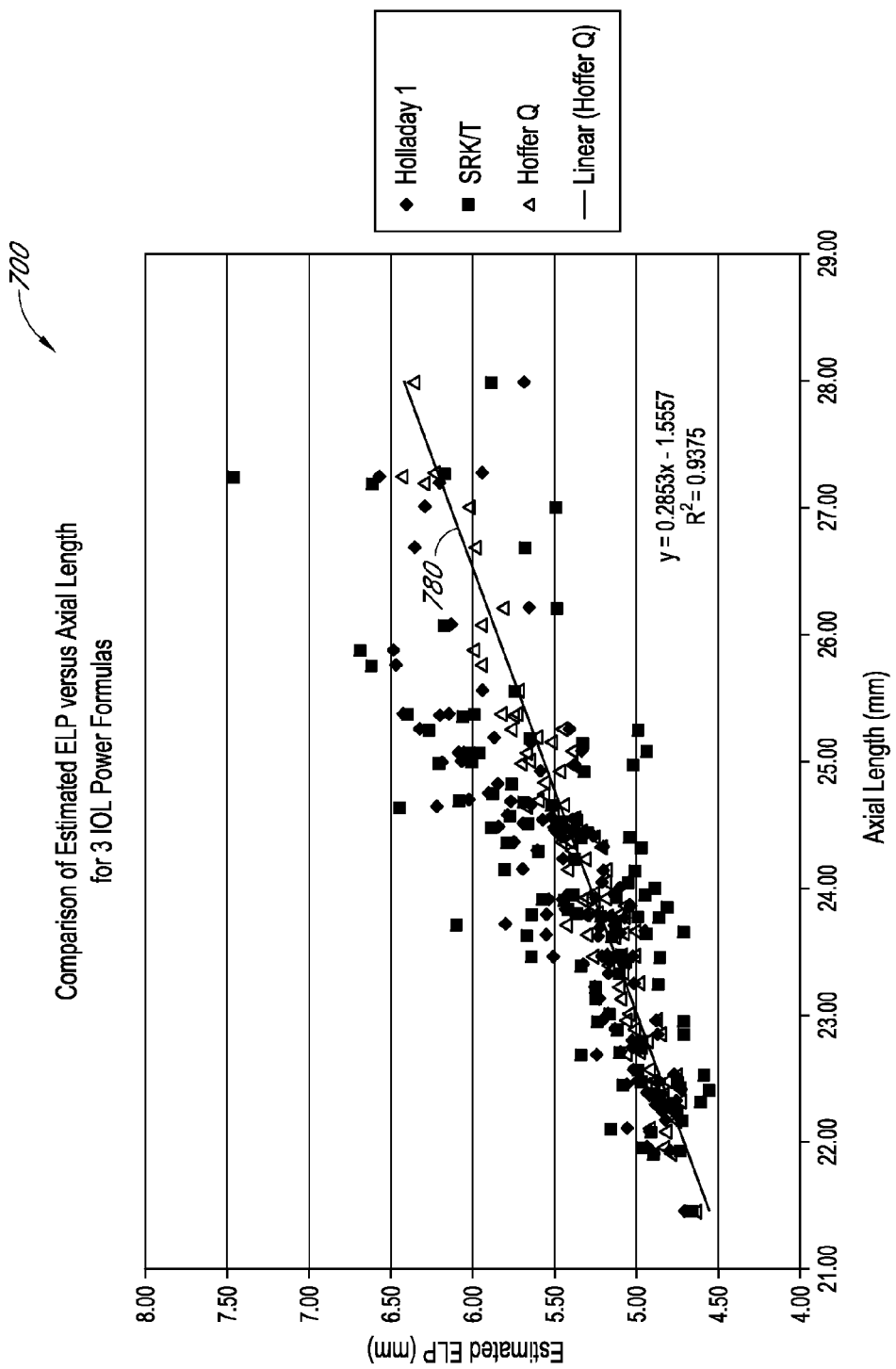
FIG. 7 is a plot of three different types of estimated ELP versus axial length, the three different types of estimated ELP being the Holladay 1 formula, the SRK/T formula, and the Hoffer Q formula.

FIG. 7 is a plot 700 of three different types of estimated ELP versus axial length, the three different types of estimated ELP being the Holladay 1 formula, the SRK/T formula, and the Hoffer Q formula. The Holladay 1 data is illustrated on the plot 700 by diamonds, the SRK/T data by squares, and the Hoffer Q data by triangles. As illustrated in FIG. 7, of the three tested ELP estimation formulas, the Hoffer Q ELP estimates exhibited the closest correlation with axial length ($R^2=0.9375$). Thus, in some embodiments, the Hoffer Q ELP estimation formula is used in the determination of the relationship between aphakic ocular power and ELP estimates. As disclosed herein, this relationship can be used to calculate an ELP estimate for an IOL to be implanted in a patient's eye given the aphakic ocular power of the patient's eye. This ELP estimate is useful in the determination of IOL power. While the Hoffer Q ELP estimation formula is used to calibrate the relationship between aphakic ocular power and estimated ELP in some embodiments, it should be understood that other ELP estimation formulas, such as the Holladay 1, Holladay 2, SRK/T, etc., can also be used for this purpose. In addition, the relationship between aphakic ocular power and ELP that is established using any given ELP estimation formula can be modified or enhanced based on, for example, another ELP estimation formula or on actual post-operative ELP measurements. As discussed herein, the indications of aphakic ocular power that are used to establish the relationship with ELP can be, for example, calculated theoretical aphakic ocular power values or actual intraoperative aphakic measurements.

In some embodiments, it may be advantageous to determine which of the various ELP estimation formulas exhibits the strongest correlation with the corneal curvature measurements. This can be done by, for example, determining the correlation between ELP estimates from the various formulas and corneal curvature, similar to what is illustrated in FIG. 7 with respect to axial length. As described herein, the selected ELP estimation formula can be used to determine a relationship between aphakic ocular power and estimated ELP, which is then useful in the determination of IOL power.

FIGS. 1-7 have illustrated, among other things, mathematical relationships between aphakic ocular power and ELP estimation values calculated for a particular type of IOL. The type of IOL can affect ELP estimates by virtue of, for example, a manufacturer-recommended constant associated with the particular IOL. The manufacturer-recommended constant may be, for example, an A-constant for the particular IOL (e.g., in the case of the SRK/T formula), the manufacturer's anterior chamber depth (ACD) (e.g., in the case of the Hoffer Q formula), etc. The equipment and procedures described herein, however, are not limited to any particular type of IOL. Therefore, it would be advantageous to calculate a mathematical relationship between aphakic ocular power (e.g., spherical equivalent aphakic ocular power) and estimated ELP that is independent from, or less dependent upon, any particular type of IOL.

A manufacturer-recommended constant for an IOL represents variations in IOL power selection and/or ELP estimation for the lens due to, for example, the lens style and material. For example, different IOLs may be made of different materials that affect its performance, or a particular IOL may have a tendency to sit differently in the capsular bag of the patient's eye (as compared to other IOLs) depending upon its structural design. The A-constant, or other manufacturer-recommended constant, of the IOL is used in ELP estimates and IOL power calculations to account for such lens-specific variations.

Figure 8:
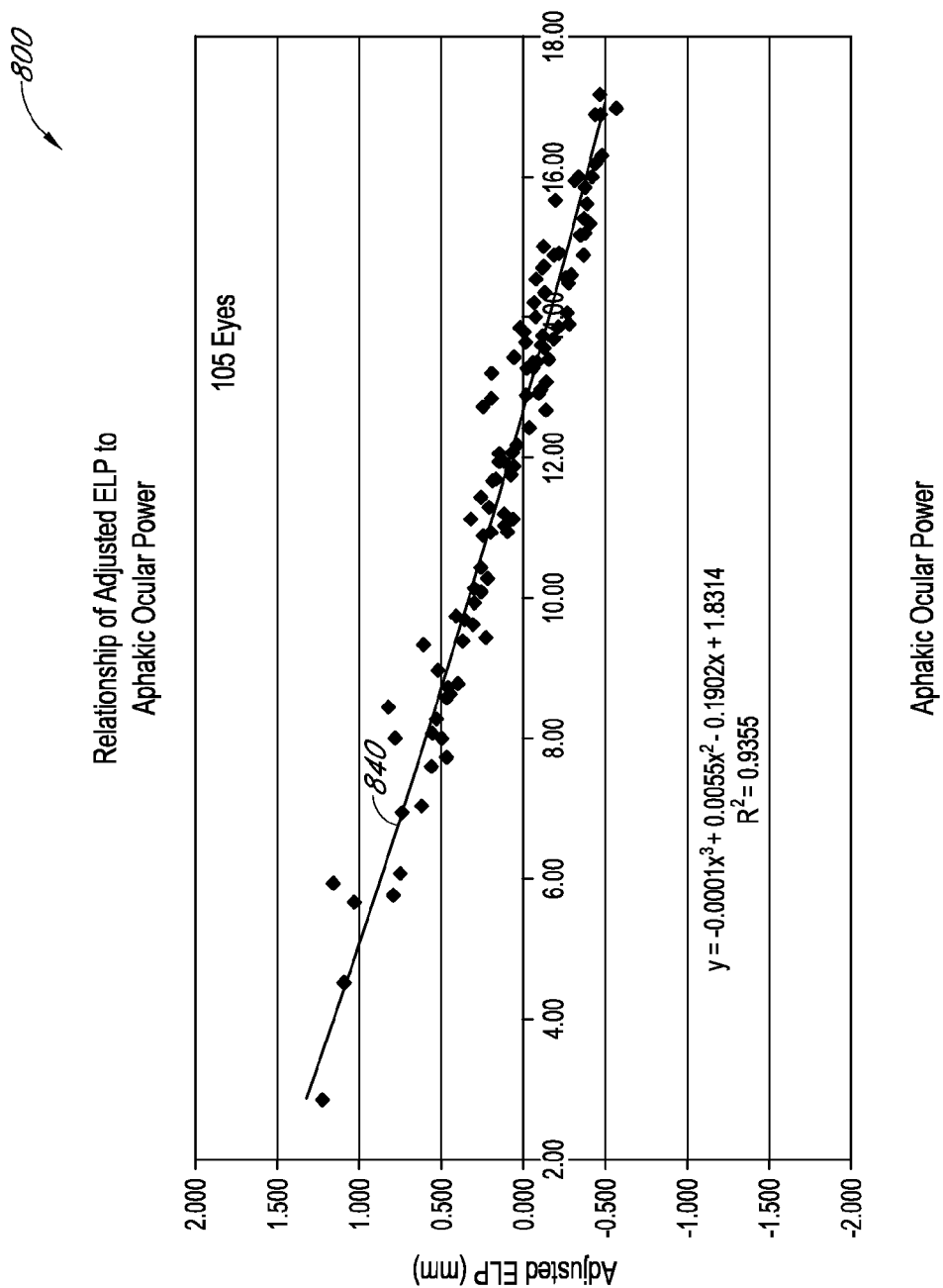
FIG. 8 is a plot of estimated ELP versus aphakic ocular power for the sample group of eyes, the estimated ELP having been determined using the Hoffer Q formula and adjusted by reducing the effect of the manufacturer's constant for the IOL on the result.

FIG. 8 is a plot 800 of estimated ELP versus aphakic ocular power for the sample group of eyes, the estimated ELP having been determined using the Hoffer Q formula and adjusted by reducing the effect of the manufacturer's constant for the particular IOL on the result. For example, the effect of the manufacturer's constant for the IOL can be substantially nulled by subtracting it from the ELP estimate. The adjusted relationship between aphakic ocular power and estimated ELP that remains can be added to the manufacturer's constant for any IOL to arrive at an IOL-specific ELP estimate for that lens and the patient's specific aphakic ocular refraction. Mathematical relationships between aphakic ocular power and estimated ELP that are derived using other ELP estimation formulas can be similarly adjusted to reduce the effect of manufacturer constants.

The adjusted ELP estimates are plotted on the axes as a function of aphakic ocular power. These values are indicated as diamonds on the plot 800. The aphakic ocular power data and the adjusted ELP estimates were correlated in order to determine a mathematical relationship between the two sets of data. In particular, a fitted curve 840 was calculated. In some embodiments, the fitted curve 840 is a cubic polynomial, as indicated in FIG. 8, though other degrees of polynomials or types of functions can also be used. The fitted curve 840 shows the empirical relationship between the aphakic ocular power data and the adjusted Hoffer Q ELP estimates for each of the eyes. Thus, the equation of the fitted curve 840 can be used to determine an adjusted ELP estimate given a particular aphakic ocular power value, the adjusted ELP estimate having reduced dependence upon, or being substantially independent from, the manufacturer's constant for any particular IOL.

The equation of the curve 840 was calculated as $y=-0.0001x^3+0.0055x^2-0.1902x+1.8314$, though the coefficients may vary depending upon the sample set of eyes and other factors. In some embodiments, the relationship between aphakic ocular power and A-constant-adjusted ELP estimates using the Hoffer Q formula can be described by a line, a quadratic polynomial, or a higher-order polynomial.

Upon comparison of the Hoffer Q fitted curve 840 to the Hoffer Q fitted curve 440 from FIG. 4, it is noted that the equations for the two curves generally differ by an additive constant of 7.0336−1.8314=5.2022. This additive constant corresponds to the manufacturer's constant for the IOL for which the ELP estimates in FIG. 4 were calculated. Thus, adjusted Hoffer Q ELP estimates calculated using the mathematical relationship given in FIG. 8 are less dependent upon any particular choice of IOL than are the Hoffer Q ELP estimates given by the relationship in FIG. 4. Accordingly, a Hoffer Q ELP estimate can be calculated from aphakic ocular power for any choice of IOL using, for example, the relationship in FIG. 8. An IOL-specific Hoffer Q ELP estimate can then be obtained by, for example, adding or subtracting the manufacturer's constant for the selected IOL. Similar adjustments for manufacturer's constants can be applied to mathematical relationships calculated to relate aphakic ocular power to estimated ELP based on other ELP estimation formulas, including the Holladay 1, Holladay 2, and SRK/T formulas.

In a similar way, the mathematical relationships between aphakic ocular power and estimated ELP can also be corrected for a surgeon factor which represents variations in IOL power calculation and/or ELP estimation due to, for example, surgical technique and the particular measurement devices used by the surgeon. Such adjustments can also be applied, for example, to mathematical relationships between aphakic ocular power and estimated ELP that are determined using actual post-surgical ELP measurements rather than ELP estimation formulas. Other factors can also be used to adjust ELP estimates.

While a relationship between ELP and aphakic ocular power can be determined by correlating aphakic ocular power values with ELP estimates calculated using estimation formulas such as those mentioned herein, this is not required. For example, a relationship between ELP and aphakic ocular power could be determined, for example, using regression analysis of measured post-operative ELP values and aphakic ocular power values (whether measured intra-operatively or calculated theoretically from other data) for a sample set of eyes. In addition, relationships can be found between ELP and aphakic ocular power in combination with one or more other ocular characteristics (e.g., white-to-white distance values). For example, regression analysis could be used to determine an empirical relationship between aphakic ocular power values and white-to-white distance values on the one hand, and ELP values (whether measured post-operatively or estimated by a formula) on the other hand. Relationships between aphakic ocular power and ELP can be found using combinations of measured and theoretical aphakic ocular power values, and combinations of post-operative measured ELP values and calculated ELP estimates.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps may be altered, added, removed, or rearranged. While certain embodiments have been explicitly described, other embodiments will become apparent to those of ordinary skill in the art based on this disclosure.

The systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on computer-readable media (e.g., optical disks such as CDs or DVDs, hard disk drives, flash memories, diskettes, or the like) that, when read by a computer or other processing device, cause it to carry out the method.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. A method for determining the optical power of an intraocular lens to be inserted into the eye of a patient, the method comprising:
   receiving as an input, from an input device, a value that indicates the aphakic refractive power of the patient's eye, wherein the input device comprises a wavefront aberrometer aligned with the patient's eye to measure the aphakic refractive power;
   determining, with a processor, an estimate of the post-surgical effective lens position (ELP) of the intraocular lens for the patient's eye, the estimate being based on the value that indicates the aphakic refractive power of the patient's eye; and
   determining an amount of optical power for the intraocular lens to be inserted into the patient's eye based on the estimate of the post-surgical ELP of the intraocular lens in the patient's eye.

2. The method of claim 1, wherein the estimate of the post-surgical ELP of the intraocular lens is further based on a relationship between aphakic refractive power and post-surgical intraocular lens ELP, and wherein the relationship between aphakic refractive power and post-surgical intraocular lens ELP is determined using regression analysis.

3. The method of claim 1, wherein the estimate of the post-surgical ELP of the intraocular lens is not based on measured corneal power of the patient's eye.

4. The method of claim 1, wherein the estimate of the post-surgical ELP of the intraocular lens is not based on measured axial length of the patient's eye.

5. The method of claim 1, wherein the value that indicates the aphakic refractive power of the patient's eye comprises an intraoperative measurement of the aphakic refractive power of the patient's eye.

6. The method of claim 1, further comprising outputting the estimate of the post-surgical ELP of the intraocular lens.

7. The method of claim 1, further comprising outputting the amount of optical power for the intraocular lens.

8. The method of claim 1, further comprising performing a measurement using the input device to determine the value that indicates the aphakic refractive power of the patient's eye.

9. An ophthalmic method for determining a relationship between post-surgical effective lens position (ELP) of an intraocular lens and aphakic ocular power, the method comprising:
   obtaining, from an input device, a plurality of values that indicate the aphakic power of a respective plurality of eyes, wherein the input device comprises a wavefront aberrometer enabled to measure the aphakic power;
   determining a plurality of values that indicate the post-surgical ELP of an intraocular lens for the respective plurality of eyes; and
   determining a relationship between the aphakic power and the post-surgical ELP using a processor.

10. The method of claim 9, wherein the plurality of values that indicate aphakic power of the respective plurality of eyes comprise a plurality of aphakic measurements of the aphakic power of the respective plurality of eyes.

11. The method of claim 9, wherein the plurality of values that indicate aphakic power of the respective plurality of eyes comprise a plurality of calculated values based on the respective corneal power and axial length of the respective plurality of eyes.

12. The method of claim 9, wherein determining the plurality of values that indicate the post-surgical ELP of an intraocular lens for the respective plurality of eyes comprises performing post-surgical measurements of the ELP for the respective plurality of eyes.

13. The method of claim 9, wherein determining the plurality of values that indicate the post-surgical ELP of an intraocular lens for the respective plurality of eyes comprises using an ELP estimation formula for the respective plurality of eyes.

14. The method of claim 13, wherein the ELP estimation formula comprises the Holladay 1, the Holladay 2, the SRK/T, the Hoffer Q, or the Hagis formula.

15. The method of claim 9, wherein determining the relationship between the plurality of values that indicate the aphakic power and the plurality of values that indicate the post-surgical ELP comprises mathematically modeling the relationship between the plurality of values that indicate aphakic power and the plurality of values that indicate the post-surgical ELP of the intraocular lens.

16. The method of Claim 15, wherein mathematically modeling the relationship comprises using regression analysis of the plurality of values that indicate the aphakic power for the respective plurality of eyes and the plurality of values that indicate the post-surgical ELP of an intraocular lens for the respective plurality of eyes to determine the relationship.

17. An ophthalmic instrument comprising:
   a measurement device for measuring the aphakic power of a patient's eye, wherein the measurement device comprises a wavefront aberrometer aligned with the patient's eye to measure the aphakic power; and
   a processor for performing a method comprising,
   receiving a value that indicates the aphakic refractive power of the patient's eye from the measurement device,
   determining an estimate of the post-surgical effective lens position (ELP) of an intraocular lens to be inserted in the patient's eye, the estimate of the post-surgical ELP of the intraocular lens being based on the value that indicates the aphakic refractive power of the patient's eye, and
   determining an appropriate amount of optical power for the intraocular lens to be inserted into the patient's eye based on the estimate of the post-surgical ELP of the intraocular lens.

18. The ophthalmic instrument of claim 17, wherein the estimate of the post-surgical ELP of the intraocular lens is further based on a relationship between aphakic refractive power and post-surgical intraocular lens ELP, and wherein the relationship between aphakic refractive power and post-surgical intraocular lens ELP is determined using regression analysis.

19. The ophthalmic instrument of claim 17, wherein the estimate of the post-surgical ELP of the intraocular lens is not based on measured corneal power of the patient's eye.

20. The ophthalmic instrument of claim 17, wherein the estimate of the post-surgical ELP of the intraocular lens is not based on measured axial length of the patient's eye.

21. The ophthalmic instrument of claim 17, wherein the value that indicates the aphakic refractive power of the patient's eye comprises an intraoperative measurement of the aphakic refractive power of the patient's eye.

22. The ophthalmic instrument of claim 17, wherein the method performed by the processor further comprises outputting the amount of optical power for the intraocular lens.

* * * * *